(12) United States Patent
Thorne, Jr. et al.

(10) Patent No.: US 8,992,505 B2
(45) Date of Patent: Mar. 31, 2015

(54) MEDICAL SYRINGE FILLING AND VALVING

(75) Inventors: Gale H. Thorne, Jr., Bountiful, UT (US); Gale H. Thorne, Bountiful, UT (US)

(73) Assignee: Thorne Consulting & Intellectual Property, LLC, Bountiful, UT (US)

( * ) Notice: Subject to any disclaimer, the term of this patent is extended or adjusted under 35 U.S.C. 154(b) by 290 days.

(21) Appl. No.: 13/597,676

(22) Filed: Aug. 29, 2012

(65) Prior Publication Data

US 2012/0323173 A1 Dec. 20, 2012

Related U.S. Application Data

(63) Continuation-in-part of application No. 13/068,529, filed on May 13, 2011, which is a continuation-in-part of application No. 13/066,565, filed on Apr. 18, 2011.

(51) Int. Cl.
| | |
|---|---|
| *A61M 31/00* | (2006.01) |
| *A61M 5/178* | (2006.01) |
| *A61M 5/00* | (2006.01) |
| *A61M 1/00* | (2006.01) |
| *A61M 5/315* | (2006.01) |
| *A61M 5/31* | (2006.01) |

(52) U.S. Cl.
CPC ... *A61M 5/31596* (2013.01); *A61M 2005/1787* (2013.01); *A61M 2005/3121* (2013.01); *A61M 2005/31508* (2013.01); *A61M 2005/31598* (2013.01); *A61M 5/31511* (2013.01); *A61M 2005/3123* (2013.01)
USPC ........... 604/518; 604/191; 604/184; 604/190; 604/231; 604/236; 604/122

(58) Field of Classification Search
USPC ......... 604/122, 184, 190, 191, 231, 236, 246, 604/207, 218
See application file for complete search history.

(56) References Cited

U.S. PATENT DOCUMENTS

| | | | | |
|---|---|---|---|---|
| 554,614 | A * | 2/1896 | Beyer | 604/236 |
| 701,671 | A * | 6/1902 | Billings | 604/125 |
| 1,367,008 | A * | 2/1921 | Bessese | 604/184 |
| 1,578,517 | A * | 3/1926 | Hein | 604/82 |
| 1,589,882 | A * | 6/1926 | Hein | 604/184 |
| 1,641,976 | A * | 9/1927 | Laurent | 604/184 |
| 2,156,023 | A * | 4/1939 | McKay | 604/184 |
| 2,643,655 | A * | 6/1953 | McKay | 604/184 |
| 2,841,145 | A * | 7/1958 | Epps | 604/89 |
| 3,729,031 | A * | 4/1973 | Baldwin | 141/2 |
| 4,067,333 | A * | 1/1978 | Reinhardt et al. | 604/191 |
| 4,153,186 | A * | 5/1979 | Nye | 222/378 |
| 4,643,721 | A * | 2/1987 | Brunet | 604/191 |
| 4,685,910 | A * | 8/1987 | Schweizer | 604/218 |

(Continued)

*Primary Examiner* — Kevin C Sirmons
*Assistant Examiner* — William Carpenter
(74) *Attorney, Agent, or Firm* — Gale H. Thorne

(57) ABSTRACT

Apparatus and methods for providing a field environment filled proximal chamber of a multi-chamber syringe and for filling a prime-free syringe are disclosed. In addition, methods for resetting valves of a multi-chamber syringe without special tools or insertion of foreign objects into the syringe are disclosed. A valve for interfacing with syringes telescopically inserted into a larger syringe and which are generally used as proximal chambers in multi-chamber syringes used in mixing and serial delivery applications is disclosed. Four embodiments of novel resettable valves are disclosed. Also, a syringe assembly for delivering a saline-dose-saline medication sequence is disclosed.

3 Claims, 12 Drawing Sheets

(56) References Cited

U.S. PATENT DOCUMENTS

| | | | |
|---|---|---|---|
| 5,032,117 A * | 7/1991 | Motta | 604/88 |
| 5,147,329 A * | 9/1992 | Brannon | 604/231 |
| 5,171,220 A | 12/1992 | Morimoto | |
| 5,298,024 A * | 3/1994 | Richmond | 604/90 |
| 5,429,610 A | 7/1995 | Vaillancourt | |
| 5,476,449 A * | 12/1995 | Richmond | 604/87 |
| 5,674,195 A * | 10/1997 | Truthan | 604/87 |
| 5,743,886 A | 4/1998 | Lynn et al. | |
| 5,779,668 A | 7/1998 | Grabenkort | |
| 5,785,682 A * | 7/1998 | Grabenkort | 604/82 |
| 6,149,628 A * | 11/2000 | Szapiro et al. | 604/191 |
| 6,602,223 B2 * | 8/2003 | Szapiro et al. | 604/89 |
| 6,997,910 B2 * | 2/2006 | Howlett et al. | 604/191 |
| 7,048,720 B1 | 5/2006 | Thorne, Jr. et al. | |
| 7,101,354 B2 | 9/2006 | Thorne, Jr. et al. | |
| 7,789,862 B2 | 9/2010 | Thorne, Jr. | |
| 7,951,108 B2 | 5/2011 | Harper et al. | |
| 2003/0040701 A1 | 2/2003 | Dalmose | |
| 2009/0018496 A1 | 1/2009 | Harper et al. | |

* cited by examiner

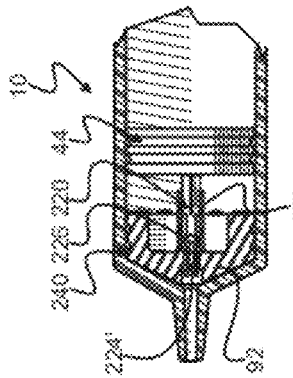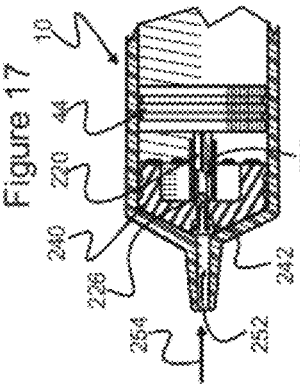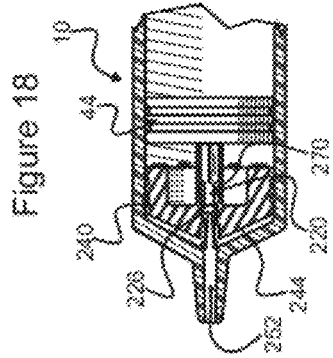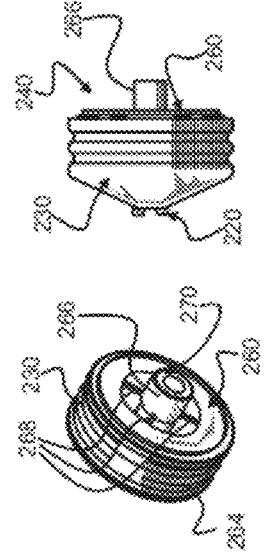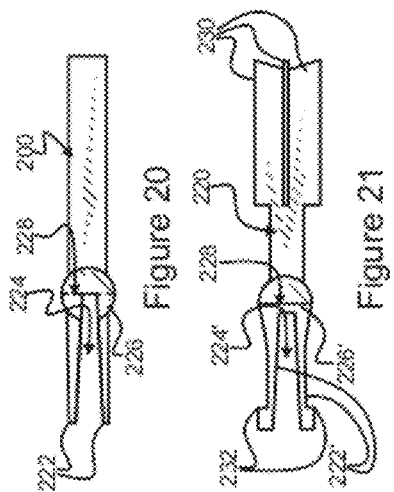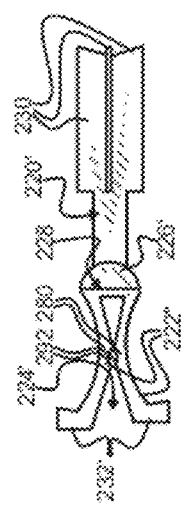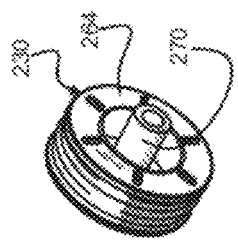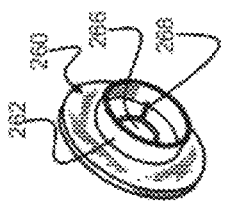

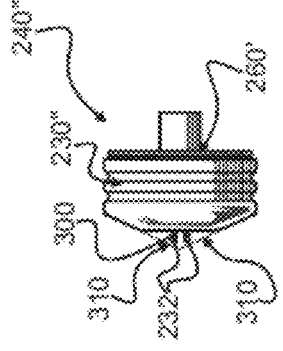
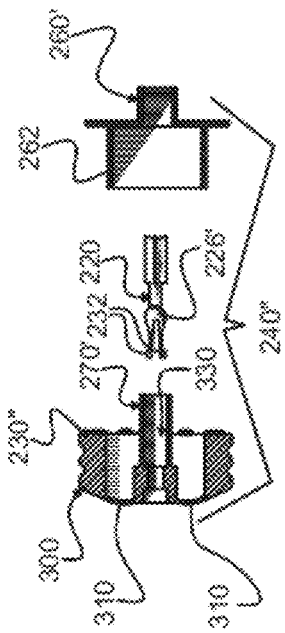
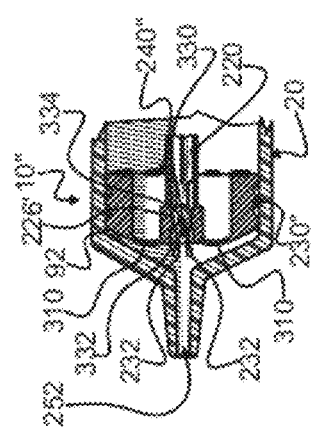
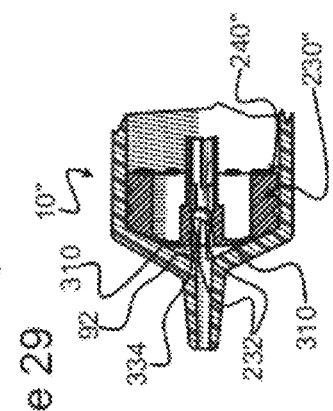
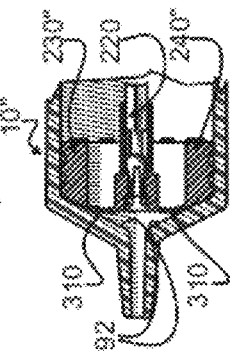
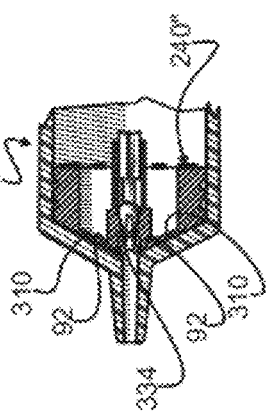
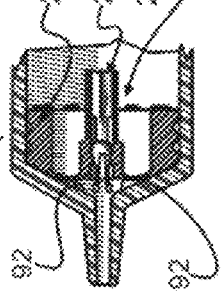

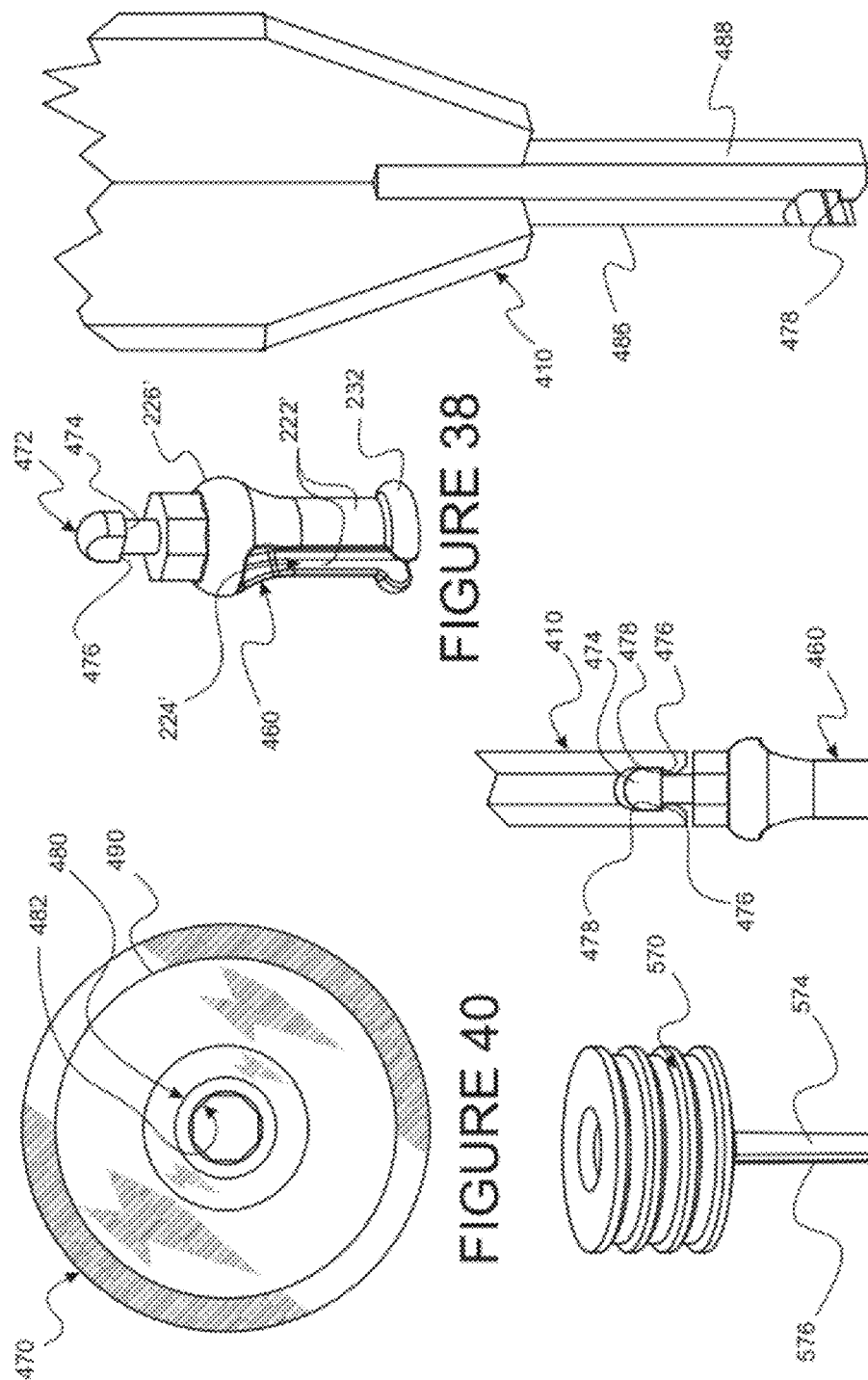

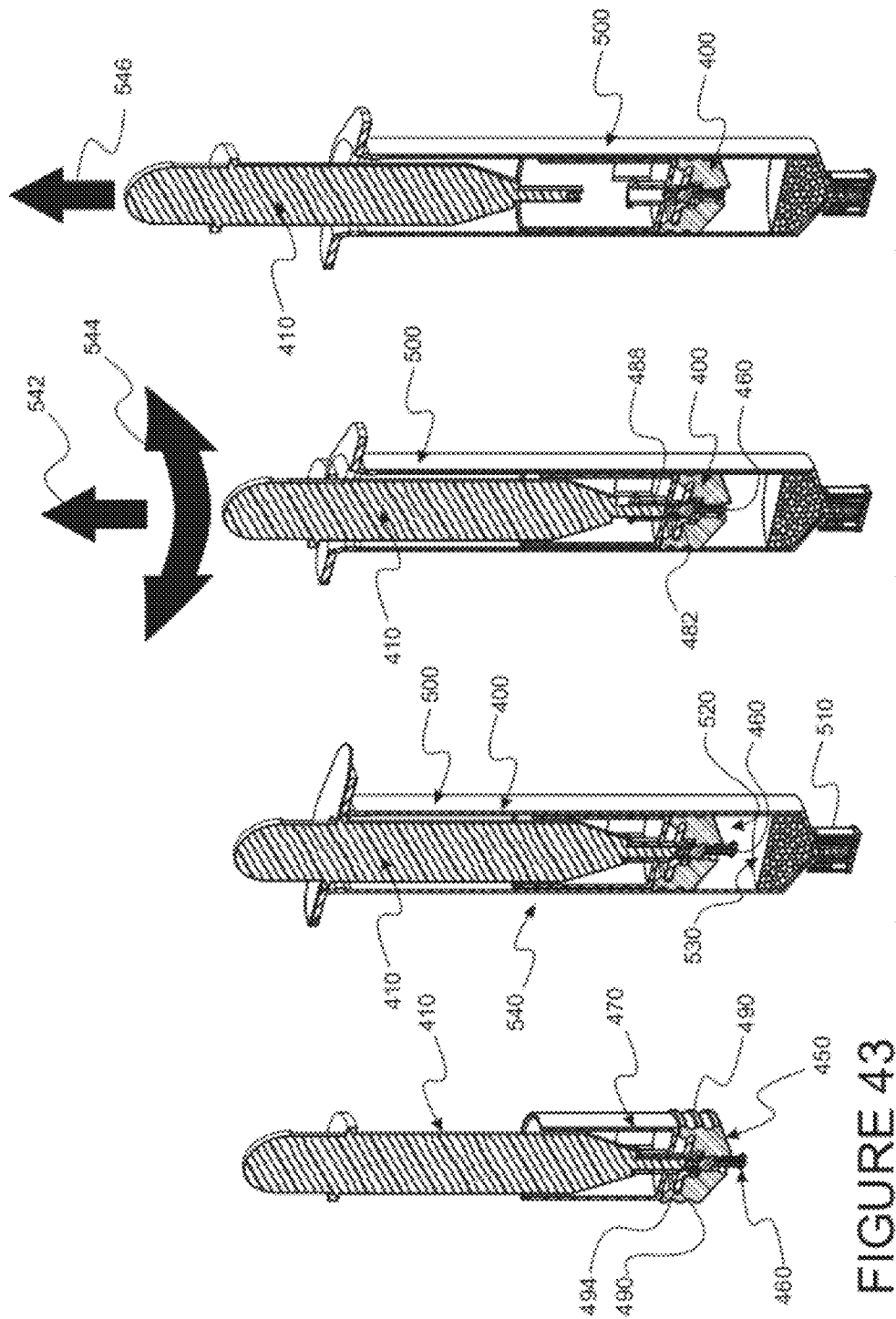

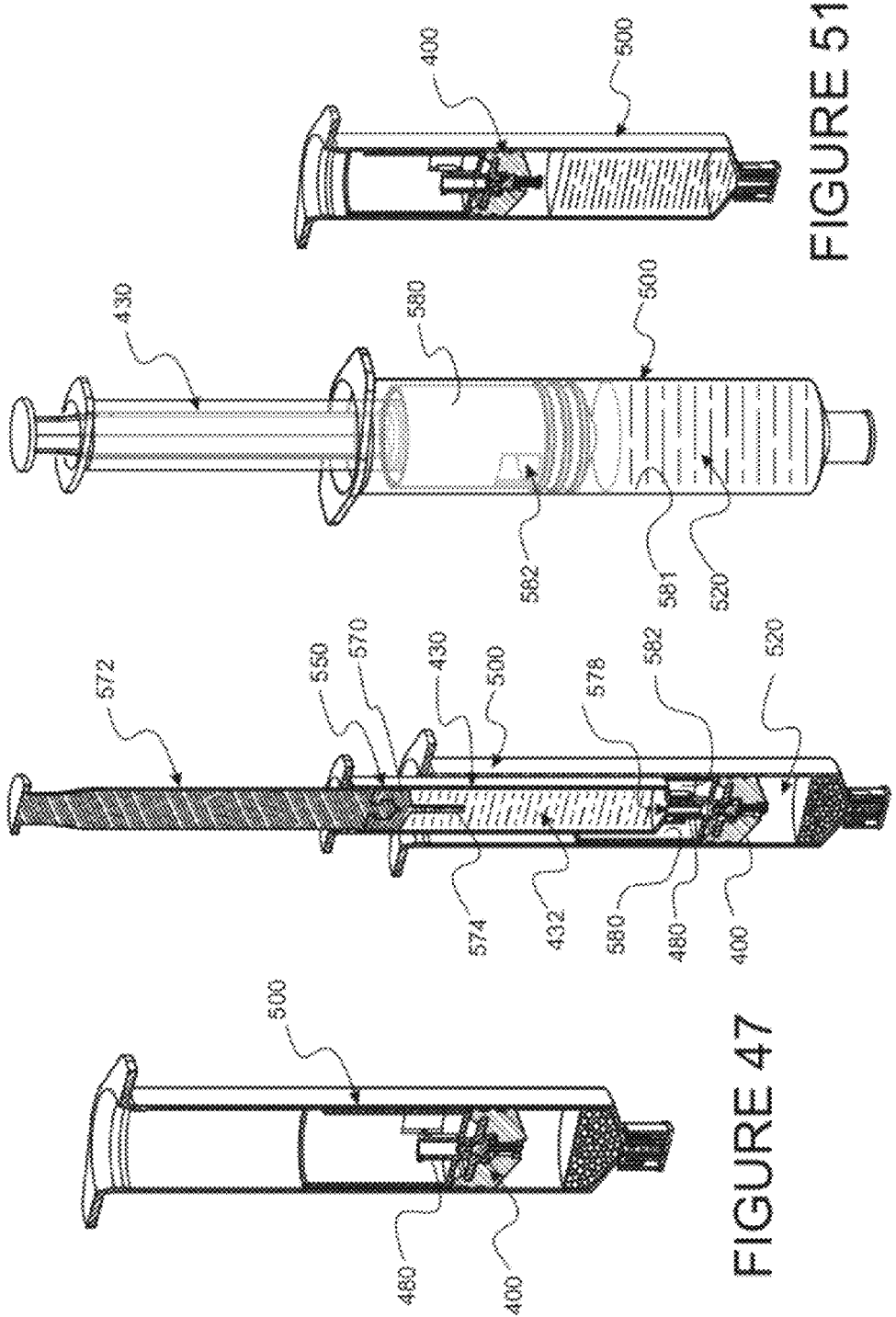

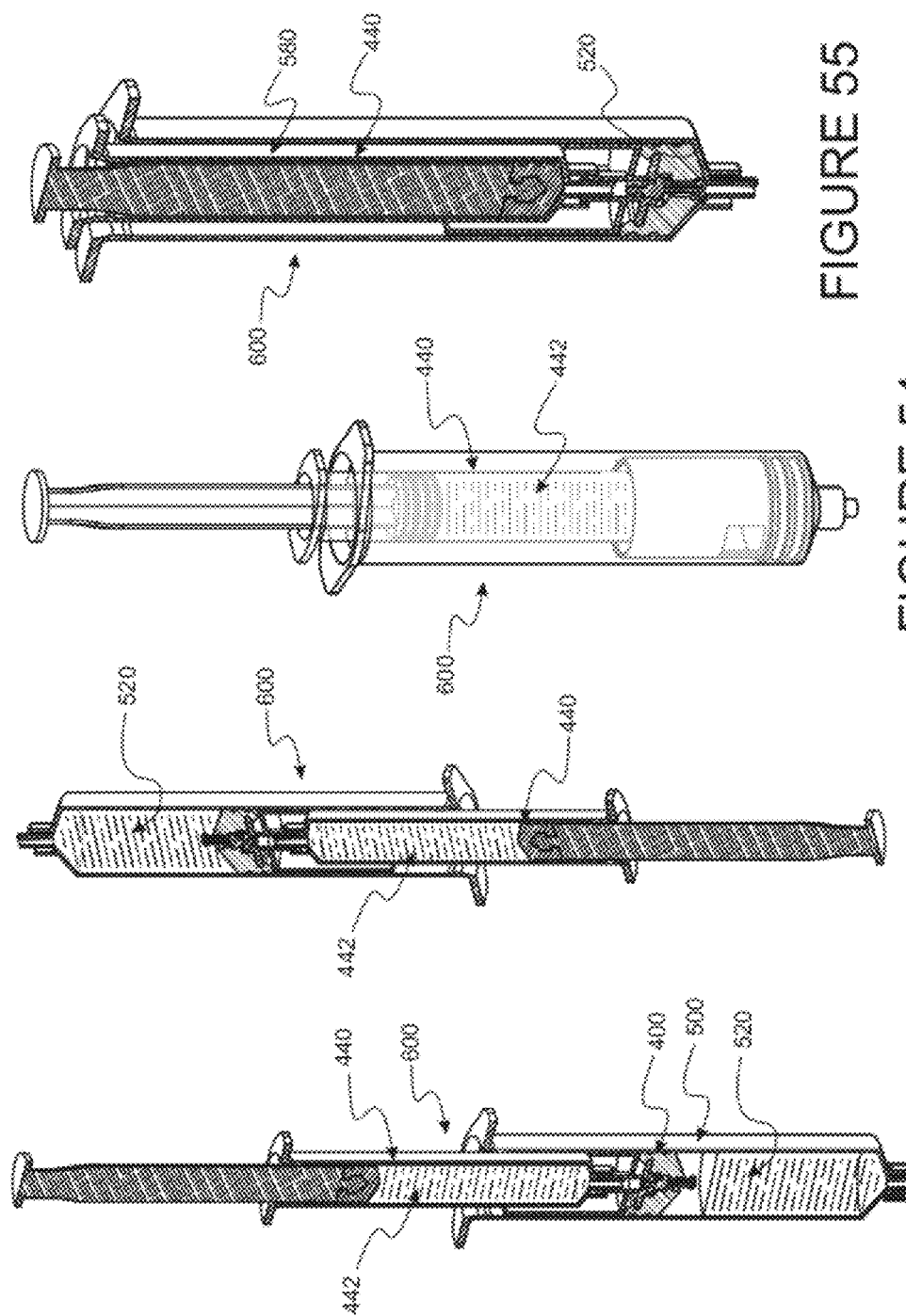

MEDICAL SYRINGE FILLING AND VALVING

CONTINUATION-IN-PART

This Patent Application is a Continuation-in-Part of U.S. patent application Ser. No. 13/068,529 titled PRESSURE ACTIVATED VALVE FOR MULTI-CHAMBER SYRINGE APPLICATIONS filed May 13, 2011 by Gale H. Thorne, Jr., et al. (Thorne 529), which is a Continuation-in-Part of U.S. patent application Ser. No. 13/066,565, titled MEDICAL SYRINGE PRIME AND CROSS-CONTAMINATION FREE DEVICES filed Apr. 18, 2011, by Gale H. Thorne, Jr. et al. (Thorne 565) which are made part of this Patent Application by reference.

FIELD OF INVENTION

This invention relates to applications for valves disposed within barrels of conventional medical syringes, and, in particular, to such valves which are used in multi-chamber and mixing syringe applications. Inventive applications, disclosed herein, include multi-chamber syringes having proximal chambers which can be accessed for filling after syringe assembly and sterilization and mixing syringes which permit variably determining final dose concentration and which provide for optional delivery of a disparate solution (such as a flush solution) prior to and following dispensing of a dose previously mixed within the syringe.

DESCRIPTION OF RELATED ART

Inventions disclosed herein relate, in general, to filling, actuating and resetting valves associated with multi-chamber dispensing and mixing syringes. Examples of multi-chamber and mixing syringes are disclosed in U.S. Pat. No. 7,789,862 B2 (Thorne 862) and Thorne 529. Disclosures associated with proximal chamber filling and associated prevention of gas delivery there from as disclosed in Thorne 862 also apply to filling of rear or proximal chambers of syringes, generally. Of course, as related in Thorne 862, gas disposed within a proximal chamber of a multi-chamber syringe should be limited to a volume which assures delivery of only liquid from the proximal chamber of a syringe.

Plunger rod or stem assemblies are commonly used for all known multi-chamber assemblies and prime free syringes (as disclosed in Thorne 565) and are disclosed in many forms and shapes. However, there are no known plunger rod or stem assemblies known to Applicants at this time which provide an opportunity for filling a proximal chamber of a multi-chamber syringe or a prime free syringe after a plunger of a plunger rod or stem assembly has been inserted into a syringe barrel to close and define that proximal chamber. In addition, there are no known multi-chamber syringe devices which replace a plunger rod assembly of a first medical syringe with another syringe and plunger rod assembly affixed through a valve disposed within the barrel of the first syringe, the other plunger rod assembly being used for displacing fluid in both syringes.

It may be noted that, providing capability for filling a proximal chamber after displacement of the plunger of a plunger rod assembly is so disposed, also allows cleaning and/or sterilization of multi-chamber syringe parts without disassembly if a valve is provided which may be reset (closed) without employing tools within the syringe barrel which adversely affect sterility. Thus, a completely assembled and sterilized multi-chamber syringe apparatus may be provided to a user in much the same manner as a conventional syringe is provided. In other words, filling both chambers may be accomplished sans any device assembly or disassembly.

While it is conventional practice in most developed countries to treat such items as medical syringes as being single-use and disposable, such may not be the case, worldwide. It may be important in areas where cost of labor is relatively low when compared to material costs, to provide methods where such items may be reused with safety and efficacy. For this purpose and for uses in mixing within a syringe, a method for resetting, without any disassembling of a multi-chamber syringe, is also disclosed herein. Also in some applications, such as use in enteral feeding, a syringe need only be well cleaned (rather than be sterilized) prior to a follow-on use.

BACKGROUND

General

Inventive elements disclosed within this application are diverse, and multi-faceted, but are all generally directed toward special applications and uses of conventional medical syringes. For purposes which are fully disclosed hereafter, one of the major elements is a valve which is used for dividing a barrel of a syringe into adjoining chambers, the valve being normally closed but optionally opened and then reset without jeopardizing syringe sterility during syringe use. Other elements include multi-chamber syringes used for sequential delivery and for mixing. As a proximal chamber of a multi-chamber syringe is generally closed to external fluid injection in an assembled device, apparatus and methods for filling the proximal chamber of an assembled multi-chamber syringe (and of a prime free syringe) are also disclosed herein. Of primary importance are elements associated with a mixing syringe and with a sequential delivery syringe which employ various forms of the valve to provide a detachable proximal chamber housed within a syringe barrel telescoped into a larger syringe barrel which comprises the distal chamber for both sequential delivery and mixing syringe use.

BACKGROUND

Multi-Chamber Syringes

The following background is provided for an understanding of operation and structure of multi-chamber syringes (which include sequential delivery and mixing syringes and associated valves and air filtering devices. Generally, syringe apparatus which is directly associated with the instant invention employs at least one conventional syringe barrel, each barrel having an internal surface which is concentrically disposed about an elongated medial axis. In such syringes, the barrel surface has an open proximal end and a distal end having a closed interior about an orifice through which fluid is conventionally transferred.

Further, a multi-chamber syringe generally may employ a plunger rod and plunger tip combination disposed to be displaced within the barrel by application of a force against the plunger rod for dislocating fluid thereby as is the case for conventional syringes.

Within the scope of the instant invention, a multi-chamber syringe is formed within a conventional syringe barrel by a valve or discharge assembly inserted within the barrel between the plunger tip and the distal end. In this manner, a proximal chamber is made available between the valve and plunger tip and a disparate distal chamber is provided between the valve and the closed interior surface.

A proximal chamber of both a multi-chamber syringe and a prime-free syringe comprises space for fluid which may comprise gas which should be limited to a predetermined volume which should be fully contained in a chamber from which liquid has been delivered, or eliminated, to assure gas is not delivered to a patient.

BACKGROUND

Sequential Delivery Syringes

In a sequential delivery syringe, a valve separating proximal and distal chambers is normally closed and is opened when contents of the distal chamber are fully dispensed. Structure of the syringe provides an advantage due to different state characteristics between gas and liquid residing within an elongated cylindrical chamber (e.g. the proximal chamber) permitting design of a valve filter which delivers only liquid from a zone within the proximal chamber which is free of gas. In accordance with the instant invention, in all syringes where only liquid is drawn from a chamber of a syringe containing both liquid and gas, a conduit (elongated tubular) sleeve disposed in communication with the liquid zone through an access portal on a proximal end of the conduit sleeve results in only liquid being discharged from that chamber.

BACKGROUND

Mixing Syringes

Generally, mixing syringes comprise two chambers in which matter within the chambers (at least one of which is usually a liquid) is kept disparate until a mixing procedure is instituted. By a wide variety of methods and apparatus, a pathway is usually provided for communication between the two chambers permitting mixing. Mixing syringes using multiple syringes are known whereby two side-by-side syringes are affixed to a mixing interface and matter is mixed as it is dispensed. Also, U.S. Pat. No. 5,372,586 discloses a mixing syringe apparatus which employs two telescoping syringes and a valve which is opened for mixing by rotating one of the syringes to open the valve. There are no known mixing syringes for which a resettable (reclosable) valve is disclosed.

DEFINITION OF TERMS

Following is a brief list of clarifying definitions for terms used in this Application:
assembly n: a device which is made from at least two interconnected parts
bi-stable adj: a descriptor for a device having two stable states
chamber n: a volumetric portion of a closed syringe barrel
close v; when referenced to a valve, disposed to stop flow, but not set to a stable state
conduit sleeve n: an elongated tube affixed to a stopper where thru liquid is discharged from a chamber of a syringe
conventional adj: sanctioned by general custom; i.e. commonplace, ordinary
disparate n: when used in conjunction with a liquid volume, a volume of liquid which is distinctly separate from another liquid volume
differential pressure ($\Box$P) n: a pressure gradient resulting from unequal pressures exerted upon opposing sides of a structure; generally as used herein, $\Box P = P_p - P_d$ (where "p" and "d" represent proximal and distal sides
distal adj: a term which depicts placement away from a reference point (e.g. away from a user of a syringe)
downstream adj: a direction which is consistent with flow out of a syringe or away from a user
field environment n: an area free of special equipment which, for example, provides guards against device or pathway contamination during a medical procedure
fluid n: a substance (e.g. a liquid or gas) which tends to take the shape of a container
front adj/n: distally disposed or a distally disposed site (e.g. the front of a syringe which comprises the barrel orifice)
gas n: a fluid which is neither solid nor liquid
liquid n: a fluid which is neither solid nor gaseous, free flowing like water
liquid zone n: a space within a syringe barrel which can only be physically occupied by liquid
medial adj: occurring away from an outer edge; disposed near the center of (e.g. disposed away from an edge or periphery and in the vicinity of a center of gravity or axis of symmetry)
$P_d$ n: pressure in a distal chamber
plunger rod n: a portion of a syringe piston apparatus, usually affixed to a plunger tip, to which force is applied to displace fluid within a syringe barrel
plunger n: a portion of a syringe piston apparatus usually affixed to a plunger rod which is slideably moved within a barrel of a syringe to displace fluid therein
prime v: to fill liquid into a cavity generally by removing air therefrom (e.g. priming a gas separator)
$P_p$ n: pressure in a proximal chamber
proximal adj: opposite of distal (e.g. a term which depicts placement nearer to a reference point)
rear adj: opposite from front (i.e. generally associated with a part of a syringe barrel which is proximal to a syringe user)
reset v; when referenced to a valve, closing a valve into a stable closed state
SDS n: a name for a regimen for providing a drug dose generally through a catheter to a patient; SDS is known to stand for Saline(Flush)-Drug(Dose)-Saline(Flush), a sequence of fluid delivery which keeps drugs disparate during delivery
state n: a mode or condition of matter, e.g. gaseous, liquid or solid
stiction n: a special case of friction; stiction being the force required to initiate motion to a resting body, esp. when that force is greater than friction associated with a moving body
stop n: an obstruction which is differentiated from friction or stiction which halts displacement of a stopper or plunger
stopper n: a plunger associated with an assembly in a syringe which divides a portion of a conventional syringe barrel into two disparate chambers; in the instant invention, the stopper providing a closed, but selectively openable pathway for liquid flow.
syringe n: a device used for injecting or withdrawing fluids
upstream adj: a direction which is against the direction of flow from a syringe (opposite of downstream)
valve stem n: an elongated part which fits within a conduit sleeve of a stopper and provides a functional part of a normally closed valve

BRIEF SUMMARY AND OBJECTS OF THE INVENTION

Inventive elements within this Application comprise modes for filling proximal chambers of assembled syringe devices, such as multi-chamber syringes and prime-free flush syringes; for apparatus and methods for resetting a valve of a multi-chamber syringe, for providing structure for support and assembly of a valve; for modes and apparatus for triggering a valve stem to change the state of a valve of a sequential delivery and a mixing syringe; and, generally, for providing novel sequential delivery and mixing syringe assemblies.

It is a primary object to provide devices and structure for use with conventional medical syringes which provide field environment filling of syringe proximal chambers.

The Valve

In a preferred embodiment for a multi-chamber syringe, a valve preferably consists of a valvular plunger, an elongated valve stem and also may have a support or luer fitting ring. The valve stem being displaced to provide a dispensing pathway for fluid flow from an associated proximal chamber. The valvular plunger generally has cylindrical exterior sides which are sized and shaped to provide a sliding seal at the interior wall interface of the syringe barrel.

For a sequential delivery syringe application in which proximal and distal chambers are disposed in the same syringe barrel, the valvular plunger is hollow, except for a distally disposed face section which is closed except for a medially disposed through hole and an elongated open tube affixed about the through hole and extending proximally to form a conduit sleeve which ends at an open portal. The portal is disposed within a liquid only zone in the proximal chamber. (Note that, as disclosed in Thorne 565, the liquid only zone is medially disposed (by physical laws) within the proximal chamber and is a natural consequence of gas being immiscible and much lighter than liquid and therefore being continuously thrust upward, against gravity, toward the highest point along the interior sides of the syringe barrel. Thereby, a gas bubble, when restricted to a predetermined volume, is physically evacuated from a medially disposed space (called the liquid only zone.) In a device configured to meet requirements of the instant invention, the liquid only zone occupies a proximally disposed space along the long medial axis of the barrel, a predetermined distance from the distal face of the valvular plunger.

Preferably, the stopper is molded of a pliant, elastic incompressible material, such as an elastomer (e.g. butyl rubber). Thus, a portion of the stopper can be displaced to a different shape when a rigid member is forcibly imposed upon that portion, but memory within the plunger material causes that portion to return to substantially the original shape when the rigid member is removed.

In selected embodiments of inventions disclosed herein, a valve stem is disposed through the conduit sleeve and through hole such that a distal end of the valve stem extends distally out of the through hole to provide an impact point between the valvular plunger and distal end of the syringe. A portion of the valve stem therefore resides within the through hole. That portion preferably comprises a bulbous section which may be fully disposed within the through hole to displace a portion of side walls of the through hole, providing a closed, sealed pathway until removed. When the distal end of the valve stem collides with the distal end of the syringe, the valve stem is forcibly displaced proximally relative to the stopper, forcing the bulbous section outward from the through hole. Constricting material about space from which the bulbous section is displaced produces additional force to expel the bulbous section from the through hole. Once the bulbous section is fully expelled from the through hole in a sequential delivery syringe in which distal and proximal chambers are disposed within the barrel of the syringe, a conduit sleeve associated with the stem and through hole are opened permitting liquid flow from the portal. Thus, the valve stem and stopper, in combination, form a normally closed valve which is opened as a bi-stable valve upon impact of the valve (and stem) with the distal end of the syringe.

Of course, it is critical that all contents of the distal chamber of the syringe be emptied before the valve opens. Such is accomplished through the use of memory of the stopper elastomer and shape of the bulbous section of the valve stem. Upon collision of the distal end of the valve stem and distal end of the barrel and following collision of the distal face of the stopper, the bulbous section is only partially removed from the through hole and the valve is not yet opened. After collision of the stopper and syringe distal end, pressure placed upon the bulbous section via the surrounding plunger material about the through hole, providing lateral differential pressures which "squeeze" the bulbous section out of the through hole, finally opening the valve.

To expedite expulsion of the bulbous section from the through hole, the bulbous section comprises a convex face toward the hole, which is accelerated from the through hole as stopper material memory shrinks the side wall of the through hole to a substantially original size and shape.

In one embodiment of a sequential delivery syringe, to assure proper disposition of the open portal in the liquid zone, the valve stem preferably comprises a set of orthogonally disposed, proximal extensions which contact the interior wall of the conduit sleeve to align the valve stem along the medial axis of the barrel. The valve stem may be made from polypropylene or other material like that from which the barrel of the syringe is made.

In summary, the valve:
provides a selective partitioning between distal and more proximal chambers of a multi-chamber syringe.
may be used in conventional (off the shelf) commercial syringes having constant diameter hollow barrels.
may be configured to deliver fluid from a liquid only zone within the proximal chamber, thereby only delivering liquid from the proximal chamber
permits the distal chamber of the syringe to be used in much the same manner as a conventional syringe prior to dispensing fluid from the proximal chamber.
provides a normally closed, bi-stable valve action which is opened only after collision between the valve and inner surface of the distal end of the syringe (upon delivery of liquid from the distal chamber) and which remains in an open state once opened.
permits the valve to open only upon stem contact with a distal end of a syringe
may be reset by displacing the valve stem distally until to bulbous portion is fully captured within the through hole
Various forms of the valve are disclosed in detail hereafter.

Proximal Chamber Filling

Generally, filling of proximal chambers of multi-chamber syringes (and other syringes which cannot be efficaciously filled through a front (or distal) orifice) imposes a requirement for filling proximal chambers before (or concurrent with) inserting an associated plunger of a plunger rod assembly. As is well known in syringe filling art, an outlet having a convex shape is utilized for purging gas (air) from a syringe front chamber. If there is a tube (such as a tube which leads to a liquid only zone) such a purging method is unusable. As an example, an alternative for filling a proximal chamber after inserting a plunger rod assembly is utilization of a bypass "straw", which is unacceptable in most field applications. Systems for filling before inserting a plunger rod assembly are known and commercially available, but are expensive and unfit for general field use.

For these reasons, aseptic filling is not readily accomplished in a "field" environment, and proximal chambers are ordinarily pre-filled before shipment to a user. As useful life of a device is often significantly longer than the period of any associated solution which may be enclosed within a syringe, term of use of such a device is generally limited. On the other hand, opportunity to field fill a proximal chamber provides a significantly wider range of applications for a multi-chamber syringe.

Instant inventions disclosed herein provide methods for filling a proximally disposed chamber of an assembled medical syringe which cannot be efficaciously filled through the distal orifice of the syringe by providing a plunger rod assembly through which fluids can be communicated. To accomplish this, a plunger is provided which closes the proximal end of the syringe barrel, to form a proximal chamber, except for a medially disposed fluid pathway which communicates exteriorly via a through hole in a plunger rod stem or via a liquid communicating fitting. In this latter case, it is preferable to provide means whereby a plunger rod is affixed following filling of the proximal chamber.

In this manner a communication pathway is provided from the proximal chamber to a fluid source outside the syringe barrel. To facilitate an aseptic delivery of liquid into the proximal chamber, a close-able connecting interface should be provided. Preferably, the interface should be a luer fitting which may be closed with a complementary cap. Using this system, a dry multi-chamber syringe or a prime-free syringe can be delivered into a user environment and efficaciously filled thereat. As an alternative one inventive embodiment of the instant invention provides for providing a proximal chamber afforded by a chamber within a second syringe directly affixed to the valve.

Accordingly, it is an object to provide apparatus and method for filling a proximal chamber of a multi-chamber syringe or a prime-free syringe after complete assembly thereof.

It is also an object to provide apparatus and method for drawing excess gas from the proximal chamber.

It is yet another object to provide apparatus and method for affixing a separate syringe to a valve, the second syringe providing the proximal chamber.

Resetting a Valvular Plunger of a Multi-chamber Syringe

Some medical applications, such as enteral feeding and mixing, provide need and opportunity for resetting and reusing a valve within a multi-chamber syringe. It is an important consideration that special tools and insertion of foreign objects into the syringe housing be as limited as possible.

Within the scope of this instant invention resetting or closing a valve may be accomplished in two ways. A first way involves a valve which is unattached to parts associated with the proximal chamber.

First Valve Closure Method

In this case, a previously opened valve may be momentarily closed by first applying force to a portion of the valve (such as the valve stem) with the plunger of an associated plunger rod assembly to displace the stem into the closing portion of a channel provided by the valve stem. Once closed, fluid pressure may be applied from a source external to the syringe through the luer fitting at the dispensing end of the syringe. This displaces the stem within the valvular plunger to reset the valve to a stable closed state.

For such to occur, the stem must be displaced to initially close the valve before contact is made between the stem and distal end of the syringe. For this reason, the stem length should be short enough to permit the duct to be closed by applying contact force from the plunger rod plunger to the valvular plunger before stem contact is made with the distal end of the syringe.

Second Valve Closure Method

If the valve is securely affixed to parts associated with the proximal chamber, and force can be applied through a plunger rod directly associated with the proximal chamber, force, directly applied through the plunger against the valve stem, results in valve closure.

It is therefore an object to provide apparatus and method for resetting a valve, of a multi-chamber syringe, actuated from a closed state to an open state without introduction of special tools or foreign objects into the barrel of the syringe.

It is a further object to provide a valvular plunger which has an elongated tube which provides a pathway from a liquid only zone, structure for supporting the elongated tube against undo distortion upon contact with a plunger assembly component.

Structure for Support and Assembly of a Valvular Plunger Used in a Sequential Delivery Syringe disposed within a Single Syringe Barrel Commonly, an elongated tube which leads from a valvular plunger in a single barrel multi-chamber syringe to a liquid only zone is formed as part of a valvular plunger. The elongated tube, so made, is flexible and generally unable to perform its intended function when impacted by another part (e.g. another plunger). For this reason, parts of two separate elements of a plunger valve comprise supporting members. A first (internal) support, for the elongated tube, can be provided by a "winged" extension affixed to a proximal end of the valve stem. A second (external) support can be provided by a hollow, cylindrical ring which closely surrounds the elongated tube.

As such, it is an object to provide support for the elongated tube which provides a communicating pathway from the valve to the liquid only zone by providing an internal support for the tube affixed to the valve stem and an external support affixed to a proximal ring support of the valvular plunger.

Latch Release for a Valve Stem of a Valvular Plunger

Using a valve stem which is actuated to open a valve by linear proximal displacement upon contact with a distally disposed face of a syringe requires a part that protrudes physically from a distal face of the valve. Such may be visually disconcerting to a multi-chamber syringe user and may lead to inadvertent valve actuation.

It is, therefore, an object to provide a valve stem which is actuated by a medially directed displacement of a stem member which is latched at the distal end of a valvular plunger.

Such latching changes dynamics of the closed state of the valve, as a bulbous portion of the valve stem need not be as deeply inserted within a pathway of an associated valvular plunger because closed state stability is dependent upon the latch rather than a balance of forces for retention of the valve in the closed state.

Triggering Latch Release Following Plunger Contact with Syringe

Also providing a valve for a multi-chamber syringe having a trigger which is actuated by displacing a valve stem upon stem contact with an internal distal face of the syringe but which comprises a valvular plunger which is formed to first collide with the syringe distal face is an object. For such, the valvular plunger comprises a flexible distal face which is deformed to permit ultimate stem contact with the distal face of the syringe and, thereby, valve triggering.

It is also an object to provide such a flexible distal valvular face which deforms upon contact with the internal syringe face to nest thereat to minimize dispensing dead space.

Luer Interfacing Valves for Mixing and Sequential Delivery

A preferred embodiment of novel valve structure associated with the instant invention comprises a valvular plunger, a valve stem and a support and gating ring comprising a fitting which is compatible with a medical syringe. Such a fitting may be a female luer fitting. Generally, the valve is disposed in a barrel of a conventional first larger syringe as part of a multiple chamber assembly. The luer fitting permits another smaller syringe to be affixed to the valve within the barrel of the first syringe and the plunger assembly of the smaller syringe to be used to displace fluid disposed within barrels of both syringes.

It should be noted that the barrel of the smaller syringe effectively becomes a proximal chamber of a sequential delivery syringe when so affixed with the valve being actuated (opened) when contents of the larger syringe barrel have been dispensed. The fitting also permits replacement of the smaller syringe with a subsequently used small syringe, thereby providing a means for field substitution of the proximal chamber. Of course, the smaller syringes can be filled by methods well known in the use of medical syringe art.

By providing a removable pull tab affixed to the valve stem through an open valve fitting, access to a "distal" chamber disposed within the larger syringe barrel may be first securely closed for shipment and storage. When preparing to mix material disposed in two chambers of the assembly, the valve is opened by pulling upon the pull tab to displace the stem to the proximal offset open position, then removing the pull tab so a smaller syringe, prefilled with a diluent, is then affixed to the fitting. For mixing, diluent from the smaller syringe proximal chamber is dispensed into the distal chamber.

It should be understood by one who is skilled in medical syringe art that the requirement for a pull tab may be eliminated by providing the valve in an open state and closing the associated pathway with a female cap which closes the path through the valve adapter. In either event, structure associated with the plunger of the smaller syringe resets the valve when fluid is fully dispensed from the smaller syringe.

After mixing is complete, the smaller syringe may be replaced by a similar syringe containing flush solution. Thus, a concentrate, such as lyophilized powder, may be reconstituted within a distal chamber of a syringe and then a proximal chamber containing flush solution may be affixed to provide first, a mixing syringe and second a sequential delivery syringe for delivery of the mixed solution followed by a flush.

It should be noted that a simple sequential delivery syringe is provided by eliminating the pull tab and supplying a disparate solution for delivery from an affixed smaller syringe which first communicates with a closed valve and with a first delivered fluid resident in the barrel of the larger syringe, then delivers the disparate solution once the valve is opened upon emptying the distal chamber. It should also be noted that when the plunger assembly of a small syringe is used to displaced the valve, only the valve plunger moves relative to an associated barrel wall. The plunger of the smaller syringe is not so displaced until the valve plunger is fully displaced to contact the distal face of the associated barrel.

It is therefore an important object to provide a valve assembly for a multi-chamber assembly which is designed to first reside in the barrel of a larger syringe and second to provide an interface whereby a smaller syringe is affixed thereto, the valve having open states for dispensing fluid from the smaller syringe into the barrel of the large syringe and closed states whereby fluids within the large and smaller syringes are kept disparate and separately dispensed.

It is a very important object to provide a sequential delivery syringe in which the distal chamber is used as a conventional single chamber syringe and the proximal chamber provides a flush which is especially significant when considering flushing a system used to deliver antineoplastic or other hazardous drugs.

It is another important object to provide a syringe assembly which is usable in a field environment for mixing and to which a flushing syringe can be affixed to provide a flush subsequent to dispensing a solution mixed within the syringe.

It is also an important object to provide a mixing syringe and a sequential delivery syringe which, when dispensed via a syringe pump, have common modes of operation.

It is a further object to configure components and valves disclosed herein and thereby provide a saline-drug-saline sequential delivery syringe assembly.

These and other objects and features of the present invention will be apparent from the detailed description taken with reference to accompanying drawings.

BRIEF DESCRIPTION OF THE DRAWINGS

FIG. 17 is a cross section similar to the cross section seen in FIG. 16, but with a plunger of a plunger rod assembly disposed into contact with a proximally exposed part of the valve stem.

FIG. 18 is a cross section similar to the cross section seen in FIG. 17, but with a plunger of a plunger rod assembly disposed to displace the valve stem distally to close the valve.

FIG. 19 is a cross section similar to the cross section seen in FIG. 18 showing the result of fluid pressure applied from a distal source through the dispensing orifice of the syringe to displace the valvular plunger about the valve stem, which is held in place by the plunger of the plunger rod assembly, thereby resetting (closing) the valve.

FIG. 20 is a magnified side elevation of a PRIOR ART valve stem.

FIG. 21 is a side elevation, similar to FIG. 20, but with a pair of feet for contact with a proximal face at a distal portion of a syringe and a tube supporting structure affixed to a proximal portion of the valve stem.

FIG. 22 is a perspective of an exemplary valvular plunger valve according to the present invention. (An associated plunger stem is not seen in FIG. 22.)

FIG. 22A is a side elevation of a fully assembled plunger valve comprising parts seen in FIGS. 21, 22 and 23.

FIG. 23 is a perspective of a support ring used with the valvular plunger seen in FIG. 22.

FIG. 24 is a perspective of a valvular plunger for a valve for a multi-chamber syringe made according to the instant invention.

FIG. 28 is a magnified side elevation of a valve stem of the plunger valve seen in FIGS. 25-27.

FIG. 29 is an exploded cross-section of a valve which is similar to valves seen in FIGS. 11, 13 and 25, but having a feature which permits initial contact between a plunger and syringe distal wall before a valve stem makes contact.

FIG. 29A is a side elevation of a fully assembled valve seen in exploded view in FIG. 29.

FIG. 30 is a cross-section of the valve seen in FIG. 29 with no valve contact against the distal end of the syringe seen in part.

FIG. 31 is a cross-section of the valve seen in FIG. 30, but with a portion of valvular plunger displaced by upstream pressure to be in contact with a proximal internal face of the syringe.

FIG. 32 is a cross-section of the valve seen in FIG. 31 with the valve stem further displaced into subsequent contact with the syringe.

FIG. 33 is a cross-section of the valve seen in FIG. 32, but with the valvular plunger distorted by displacing pressure from a plunger rod assembly to further displace a portion of the valvular plunger distally to ultimately displace the valve stem from confinement within an associated hollow, cylindrical pathway in the valvular plunger.

FIG. 34 is a cross-section of the valve seen in FIG. 33 with the valve stem further displaced by elastic decompression of valvular plunger material about the pathway in which a stem is being displaced.

FIG. 35 is a cross-section of the valve seen in FIG. 34 with the valvular plunger relaxed to an original state (as seen in FIGS. 20 and 30).

FIG. 38 is a magnified perspective of the stem seen in FIG. 37.

FIG. 39 is a magnified perspective of a connecting portion of the stem puller seen in FIG. 37.

FIG. 39A is a side elevation wherein the stem seen in FIGS. 37 and 38 is securely, but releasably, affixed to the stem puller seen in FIG. 39.

FIG. 40 is a distally facing elevation of a luer fitting adapter seen in FIG. 37.

FIG. 43 is a cross section of a fully assembled valve comprising parts seen in FIG. 42 with stem puller there-to affixed.

FIG. 44 is a cross section of the fully assembled valve, seen in FIG. 43, disposed in a conventional syringe barrel.

FIG. 45 is a cross section of the fully assembled valve and syringe barrel seen in FIG. 44 with the stem puller displaced to pull the stem to open the valve.

FIG. 46 is a cross section of the valve and syringe barrel seen in FIG. 45 with the stem puller detached and displaced from the rest of the valve assembly.

FIG. 47 is a cross section of the valve and syringe barrel seen in FIG. 46 with the stem puller fully removed.

FIG. 48 is a cross section of the valve and syringe barrel with a small syringe containing diluent affixed to the luer fitting adapter.

FIG. 49 is a magnified perspective of a plunger part of a plunger rod assembly seen in FIG. 48.

FIG. 50 is a perspective of the valve, syringe barrel and small syringe, seen in FIG. 48, with diluent seen dispensed from the small syringe into the barrel containing the valve.

FIG. 51 is a cross section of the syringe barrel seen in FIG. 50 with the small syringe (seen in FIG. 50) detached and displaced from the luer fitting adapter.

FIG. 52 is a cross section of the barrel comprising the valve assembly and mixture seen in FIGS. 50 and 51 and a small syringe affixed to the luer fitting adapter.

FIG. 53 is a cross section of the combination seen in FIG. 52 inverted to permit purging of gas from the distal chamber disposed in the barrel containing the valve.

FIG. 54 is a perspective of the combination seen in FIG. 53 wherefrom the mixture has been dispensed.

FIG. 55 is a cross section of the combination seen in FIG. 54 wherefrom the flush has also been dispensed.

DETAILED DESCRIPTION OF THE ILLUSTRATED EMBODIMENTS

Figure 1:
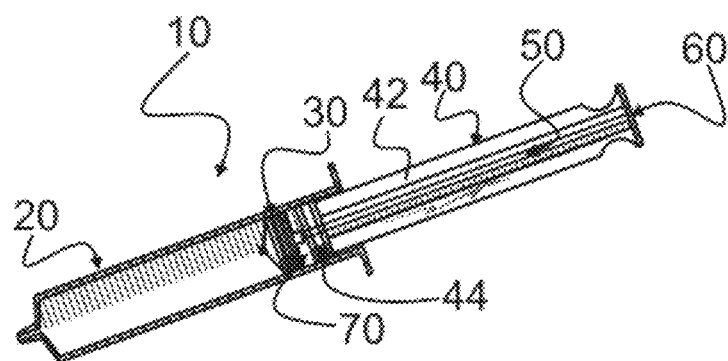
FIG. 1 is a cross section of a multi-chamber syringe with a flow through plunger rod assembly made according to the present invention but without providing a liquid fitting on the proximal end, thereof.
Figures 41, 42, 56:
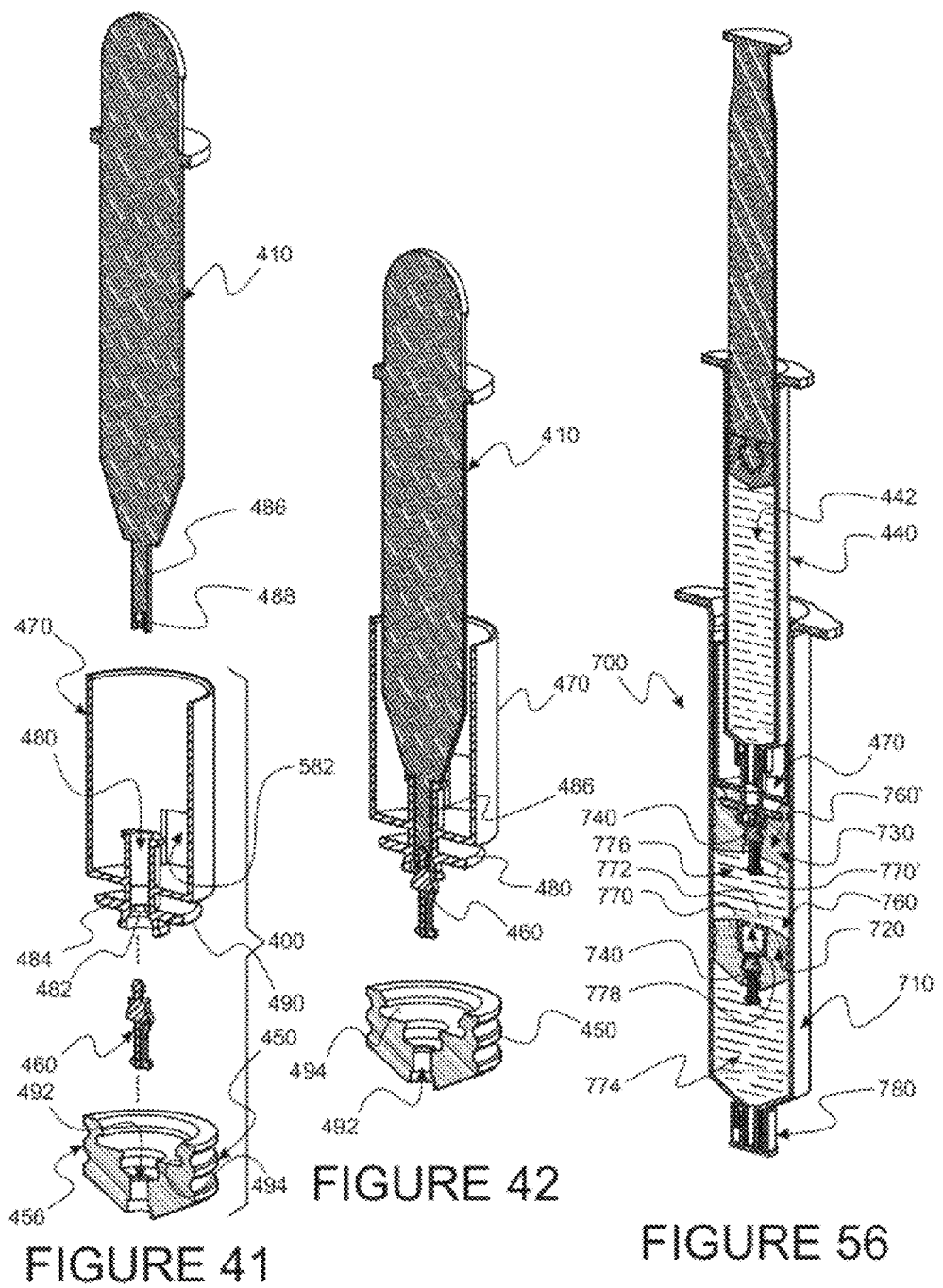
FIG. 41 is a magnified cross section of the plunger part, the valve stem, the luer fitting adapter and the stem puller seen in FIG. 37.
FIG. 42 is a cross section of a partially assembled valve comprising parts seen in FIG. 41.
FIG. 56 is a cross-section of a three chamber syringe assembly, one chamber being provided by a small affixed syringe affixed to a luer adapter assembly.

Reference is now made to embodiments illustrated in FIGS. 1-56 wherein like numerals are used to designate like parts throughout. In this description, primes of numbers are used to represent parts which are similar, but not identical to other parts having the same numbers.

Rear Chamber Filling

Apparatus and methods for filling a multi-chamber syringe is seen in various forms in FIGS. 1-9. In Thorne 862, a rear chamber of a multi-chamber syringe is disclosed to be filled before inserting a plunger of a plunger assembly into a barrel of a syringe. Similarly, in Thorne 565, a barrel of a prime-free syringe is taught to be filled before inserting such a plunger assembly. As is well understood in the syringe filling art, such insertions can be accomplished using contemporary filling equipment. However, such filling equipment is costly compared to filling equipment currently in use for pre-filled syringes. Also, requiring such insertion of a plunger assembly, after filling, restricts opportunity for providing a fully assembled, but empty, multi-chamber syringe for sale to an end user.

As seen in FIG. 1, a multi-chamber syringe 10 is fully assembled. Syringe 10 comprises a conventional syringe barrel 20, a plunger valve 30 and a plunger assembly 40 (with a plunger rod 42 and an associated plunger 44) which provides a fluid communicating pathway 50 for communication through an exteriorly disposed orifice 60 (an interconnecting fitting is not shown in FIGS. 1-3, but seen in detail in FIGS. 7-10) into a proximal chamber 70 of syringe 10.

Figure 2:
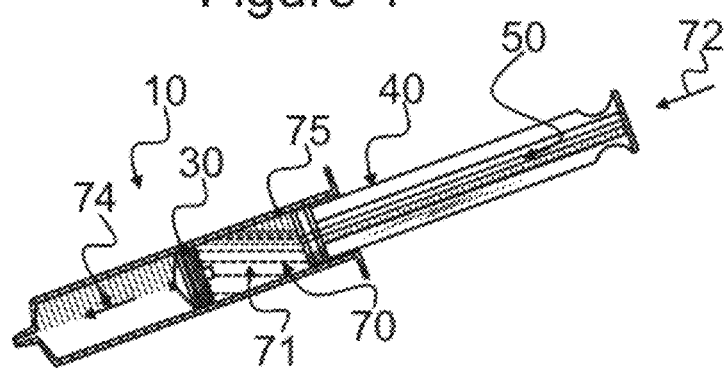
FIG. 2 is a cross section of a multi-chamber syringe, similar to FIG. 1, but with liquid dispensed through the plunger rod assembly into a proximal chamber of the multi-chamber syringe.

Chamber 70, seen in FIG. 2, is filled with fluid (most likely flush liquid) by providing liquid 71 (in direction of arrow 72) at a sufficient pressure to displace plunger valve 30 distally (in direction of arrow 74). Excess gas 75 may be withdrawn by vertically orienting syringe 10 with plunger assembly 40 superiorly disposed, as is well known and understood in the syringe handling art.

Figures 3, 3A:
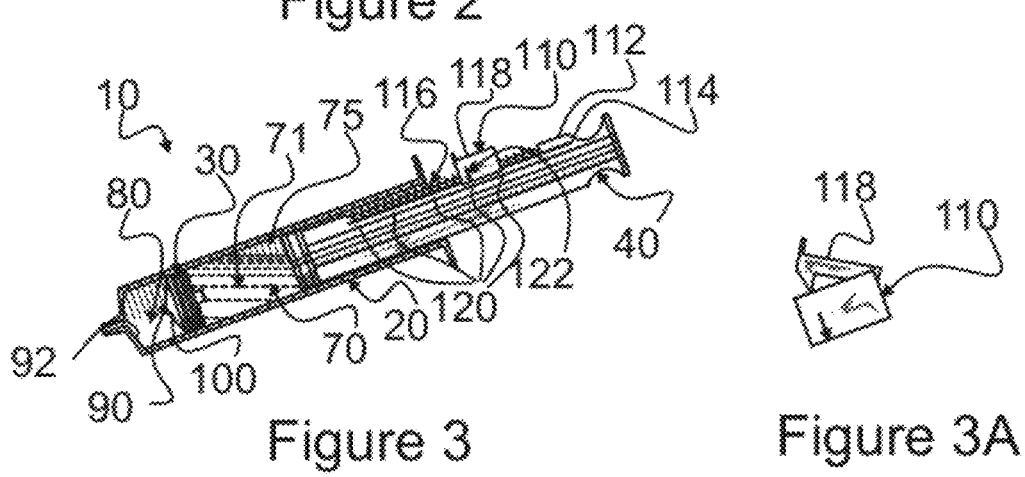
FIG. 3 is a cross section of a multi-chamber syringe, similar to FIG. 2, but with a latching stop assembly affixed to a portion of the plunger rod assembly.
FIG. 3A is a magnified side elevation of a housing with a pawl associated with the stop assembly seen in FIG. 3.

Now referencing FIG. 3, a front or distal chamber 80 may be filled as a chamber of a conventional syringe is filled. However, it should be noted that a valve stem 90 of plunger valve 30 is distally exposed relative to a valvular plunger 100 (for valve actuation which is disclosed in detail hereafter). Such exposure, if not properly taken into account, may lead to valve actuation upon inadvertent contact with internal distal face 92 of barrel 20. By incorporating a variable stop 110 along a rib 112 of plunger assembly 40 as seen in FIGS. 3 and 3A, such inadvertent actuation may be obviated.

Stop 110 may be formed to be displaced along a premolded track 114. A plurality of ratchet teeth (generally numbered 116) are exposed along one side of rib 112 with a displaceable pawl 118 (See FIG. 3A) providing a variably settable stop. Note that a plurality of indicia 120 which are disposed to indicate a position for stop arrow 122. The indicia provide a volume indicator value for the volume of liquid dispensed into chamber 70.

Figure 4:
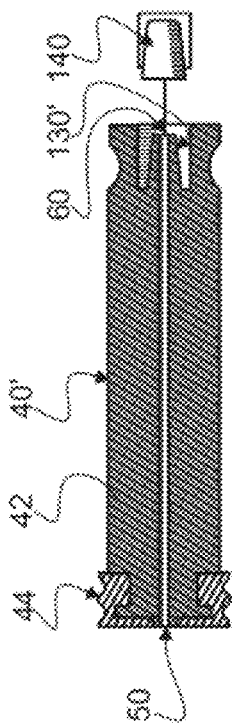
FIG. 4 is a magnified cross section of a plunger rod assembly according to present invention with a male luer fitting provided on the proximal end.

One plunger rod assembly 40 is seen in FIG. 4 comprising a molded rod 42 with an associated plunger 44. Note that fluid communicating pathway 50 continues through plunger 44. At orifice 60 a male luer fitting 130 provides conventional attachment for a luer fitting and for liquid source attachment and for a cap, such as cap 140 (which is an example of a commonly available male luer cap).

Figure 5:
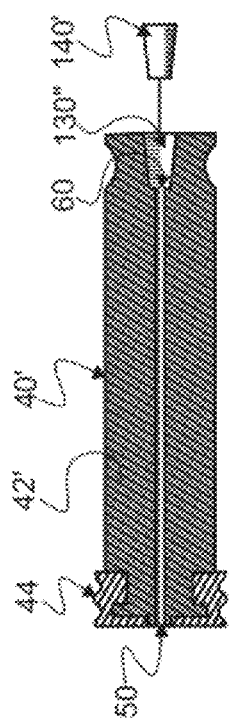
FIG. 5 is a magnified cross section of a plunger rod assembly according to the present invention with a female luer fitting provided on the proximal end.

Other fitting attachments may also be used within the scope of the instant invention. For example, as seen in FIG. 5, a plunger rod assembly 40' is seen to comprise a female luer fitting 130' which is closed by a female luer cap 140'. In the cases of both FIGS. 4 and 5, plunger 44 must provide two seals, a first seal at the barrel wall of a surrounding syringe barrel and for assuring there is no fluid flow medially other than through pathway 50.

Figure 6:
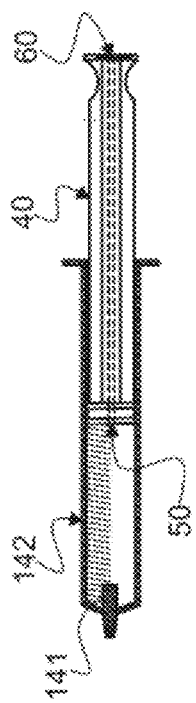
FIG. 6 is a cross section of a prime-free syringe, according to the present invention, with a flow through plunger rod assembly made according to the present invention, a fitting similar to fittings seen in FIGS. 5 and 6 is preferred, but not seen therein.

As one who is skilled in the syringe filling art understands, it is difficult to fill a prime-free flush syringe with a distally disposed hollow tube 141 which accesses a liquid only zone (see FIG. 6). A plunger rod assembly 40 provides for filling a prime-free flush syringe 142, as seen in FIG. 6, via a pathway 50.

Commonly, filled syringes are often provided for patient area use from medical vending machines with attachable plunger rods provided separately to keep stored item length short.

Figure 7:
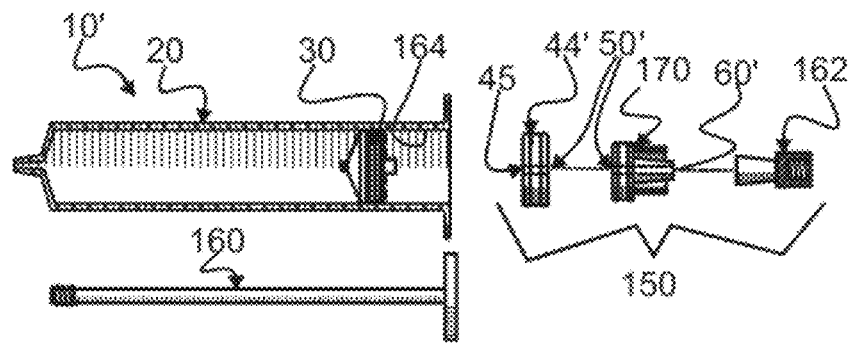
FIG. 7 is a cross-section of a multi-chamber syringe with a flow through plunger rod assembly made for a medical vending machine application, parts of the plunger rod assembly being seen in exploded format.
Figure 8:
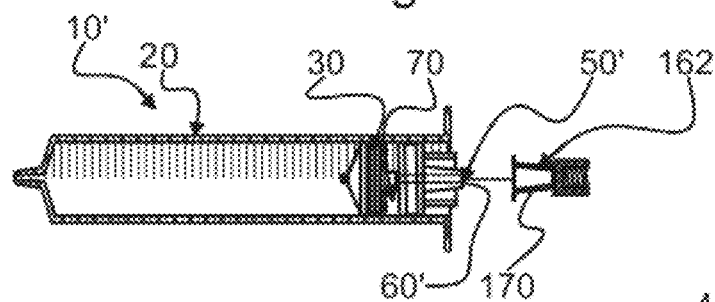
FIG. 8 is a cross section of the medical syringe seen in FIG. 7 with plunger parts assembled into the barrel of the syringe.
Figure 9:
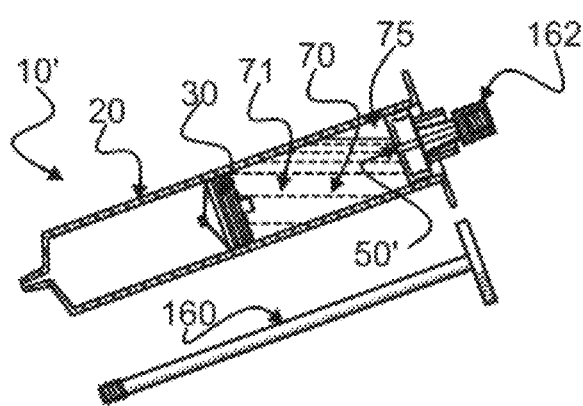
FIG. 9 is a cross section of the medical syringe seen in FIG. 8 with a cap applied to close access to the barrel of the syringe following dispensing liquid into the proximal chamber.

Reference is now made to FIGS. 7-9 wherein such a dual chamber syringe 10' is seen to comprise a conventional syringe barrel 20, a plunger valve 30 and a plunger assembly 150 which provides a fluid communicating pathway 50' (see FIG. 9) for communicating through an exteriorly disposed orifice 60' (enumerated in FIG. 7) to fill a proximal chamber 70 (See FIGS. 8 and 9). A separate, attachable plunger rod 160 is seen adjacent to barrel 20 in FIGS. 7 and 9.

As seen in FIG. 7, plunger assembly 160 comprises a plunger 44' with a medial fluid flow orifice 45, an associated feed-through fitting 170 and a cap 162. Plunger 44' is designed to wipe fluid while being displaced from the inside wall 164 of barrel 20 as is well known in the medical industry; however, in this case, plunger 44' also is designed to provide a leak-free interface along pathway 50' with fitting 170 which also provides a portion for pathway 50' (the proximal chamber 70 filling pathway seen in FIG. 9). A cap 162 is provided to close pathway 50' after filling.

An assembled, empty proximal chamber 70 is seen in FIG. 8. As noted supra, while fitting 170 is seen to be a male luer fitting, other medical fittings may be used within the scope of the instant invention.

As seen in FIG. 9, liquid 71 has been dispensed into chamber 70, displacing valve 30 distally. Also, a limited amount of gas 75 (likely air) remains in chamber 70. Of course, the gas remaining should not exceed a volume which would result in delivery of anything but liquid from chamber 70. Note, that a desired amount of such gas may be withdrawn from chamber 70 by orienting syringe 10 vertically and applying a less-than-atmospheric pressure to pathway 50'.

Figure 10:
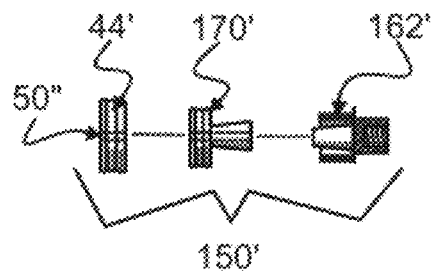
FIG. 10 is an exploded view of a multi-chamber syringe flow through plunger rod assembly comprising filling attachment parts of a flow through plunger, a flow-through female luer fitting and a cap.

Feed through fittings may be used in many forms within the scope of the instant invention. As an example, an exploded view of an alternate set of plunger assembly 150' parts is seen in FIG. 10. Plunger assembly 150' comprises a valvular plunger 44', an associated feed-through, female luer fitting 170' and a cap 162'. Plunger 44' provides a leak-free interface with fitting 170' and a continuation of pathway 50" (the proximal chamber 70 filling pathway). Cap 162' is provided to close pathway 50" after filling.

Materials used for rigid parts (e.g. valve stems, caps, plunger rods, etc.) may generally be the same material from which syringe barrel 20 is made (i.e. polypropylene, glass, etc.). Plungers should be made from the same material tested and approved for medical syringes (e.g. butyl rubber).

Valve Actuation

Figure 11:
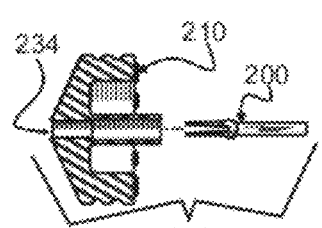
FIG. 11 is a cross-section of a PRIOR ART representation of a valvular plunger shown in cross section and an associated plunger stem.
Figure 12:
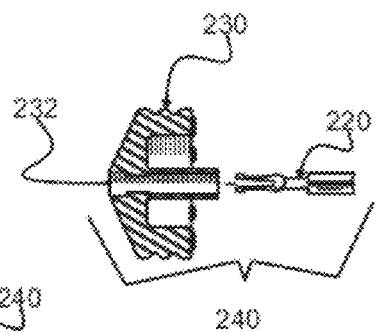
FIG. 12 is a cross section of valvular plunger made according to the present invention and an associated plunger stem also made according to the present invention.
Figure 12A:
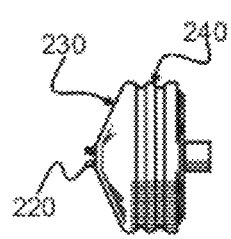
FIG. 12A is a side elevation of an assembled valve comprising parts seen in FIG. 12.

Reference is now made to FIGS. 11-24. A stem 200 and valvular plunger 210 for a valve 212 disclosed as PRIOR ART in Thorne 862 is seen in FIG. 11. A stem 220 and a valvular plunger 230 of an embodiment of a plunger valve 240 of the instant invention is seen in FIG. 12 (Note: a support ring, disclosed in detail hereafter, is not shown in FIG. 12 for clarity of presentation). A fully assembled valve 240 is seen in FIG. 12A. The primary difference between plunger 210 and plunger 230 is a distally disposed cavity 231 of greater diameter than a distally disposed channel 234 in plunger 210 (see FIG. 11) being provided in plunger 230. The purpose for the increased cavity is disclosed in detail hereafter.

A pair of magnified stems 200 and 220 are seen in FIGS. 20 and 21, respectively. In FIG. 20, stem 200 is seen to comprise a pair of legs (generally numbered 222) which are separated to provide a duct 224 for fluid flow. Note that duct 224 opens within a bulbous portion 226 of stem 200 along a mid-plane 228 of bulbous portion 226. With such geometry, duct 224 may be opened for fluid flow when legs 222 are yet in contact with a colliding portion of a distal face of an associated syringe. (An occurrence which triggers an associated valve [e.g. valve 212] to an open state).

Stem 220, made according to the instant invention and seen in FIG. 21, has three primary differences from stem 200. The first difference is a duct 224' which is opened between legs, generally numbered 222', distally from a mid-plane 228 in bulbous portion 226'. Duct 224' opening is disposed a sufficient distance distally from mid-plane 228 to permit closure of duct 224' within an associated valvular plunger 230 (see FIG. 12) before legs 222' contact a distal face 92 (see FIG. 3) of an associated syringe. In this manner, an associated valve can be closed (by closure of duct 224') without an interfering and constraining collision between legs 222' and face 92 of the associated syringe, the reason for which is disclosed in detail hereafter.

A second difference is an added set of fins (generally numbered 230) which are sized and disposed to act as a stabilizing guide within an elongated tube 234 (see FIG. 2) of an associated valvular plunger 230, reasons for which are also disclosed hereafter. A third difference is a pair of feet 232, each one being disposed on the distal end of a leg 222' to deter any portion of stem 220 from entering into (and obstructing fluid flow of) a distal dispensing orifice of the associated syringe.

Figures 13, 15:
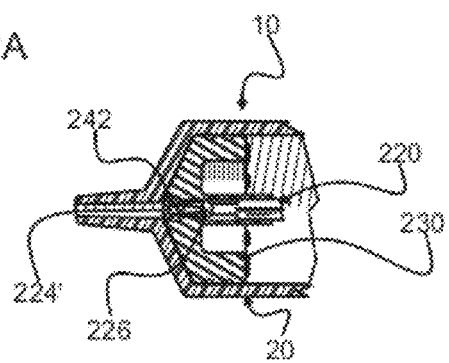
FIG. 13 is a cross section of an assembled valve made according to the present invention, the valve being proximally offset from a distal end of an associated syringe, seen in part.
FIG. 15 is a cross section similar to the cross section seen in FIG. 14, but with the valvular plunger displaced to contact the distal end of the syringe and being more distally displaced relative to the valve stem.

Reference is now made to FIGS. 13-16 wherein various steps associated with actuating (opening) a valve is provided. As seen in FIG. 13, valve 240 is assembled by displacing stem 220 into a tightly fitting channel 242 of valvular plunger 230, until bulbous portion 226 of stem 220 is held stable thereat. Note that duct 224' (and therefore valve 240) is closed thereby. Feet 232 extend distally to sense collision with a distally disposed proximal face 92 of associated syringe barrel 20 (see in part in FIGS. 13-16). In this state valve 240 is displaceable and front or distal chamber 243 of syringe 10 may be employed as a conventional chamber of a medical syringe.

Figure 14:
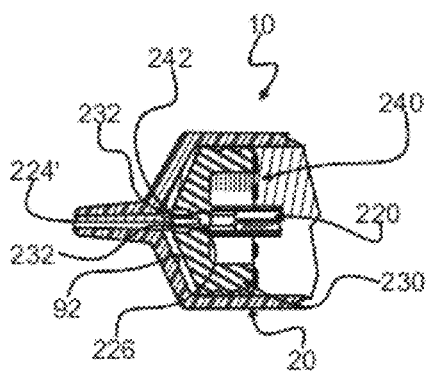
FIG. 14 is a cross section similar to the cross section seen in FIG. 13, but with a leading edge of a valve stem displaced into contact with the distal end of the associated syringe.
Figure 16:
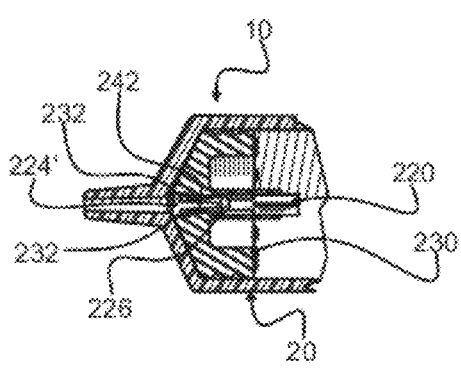
FIG. 16 is a cross section similar to the cross section seen in FIG. 15, but with valve stem displaced proximally to open the valve.

In FIG. 14, valve 240 is displaced distally until feet 232 contact proximal face 92. Continued distal displacement of valve 240 forces stem 220 and bulbous portion 226 to a point of instability relative to channel 242 (better seen in FIG. 15) and therefore, due to elasticity and incompressibility of valvular plunger 230 material, stem 220 is accelerated proximally to the state seen in FIG. 16 where duct 224' is freed from channel 242 and, therefore, valve 240 is open to fluid flow.

Resetting (Closing) Valve

Once opened, and chamber 70 (see FIGS. 2 and 3) is substantially emptied of liquid, a plunger 44 (or 44') of an associated plunger assembly may be displaced to contact stem 220 as seen in FIG. 17 (plunger rod 40 or 40' is not shown for clarity of presentation). Additional displacement, seen in FIG. 18, displaces stem 220 (and duct 224') until duct 224' is obstructed within channel 242 (before stem 220 again collides with face 92 of a multi-chamber syringe 10). So disposed, if plunger 44 is held in contact with stem 220 and pressurized fluid is forced into syringe 10 through syringe orifice 252 as indicated by arrow 254 in FIG. 18 valve 240 is reset as seen in FIG. 19. With valve 240 reset, a cycle of reuse may be initiated. Note, with valve open and a chamber 70 fillable configuration as seen in FIGS. 1-5 and 7-9, a syringe may be cleaned before reuse by methodology well known in the medical art.

To further stabilize valvular plunger 230, seen in FIGS. 12 and 22, for displacement within a syringe barrel and for resetting actions, a ring 260, better seen in FIG. 23 is used. Ring 260 is provided with two support tubes. A larger first tube 262 is disposed to provide support inside cylindrical side-wall 264 (see FIG. 22) of valvular plunger 230. A second tube 266, affixed to tube 262 by a plurality of inwardly distending legs (generally numbered 268) provides support for that tubular portion 270 of valvular plunger 230 which comprises the hollow tube which defines a channel 242 which provides a pathway to the "liquid only" zone and is used to keep portion 270 and stem 220 stable when impacted by plunger 44 (see FIGS. 17-19).

Alternate Valve Embodiments

It may be noted that feet 232 of valve 240 extend well distally from valvular plunger 230 (see FIG. 13) to determine site of collision with an associated syringe and may be subject of some concern regarding inadvertent triggering of valve 240. Reference is now made to FIGS. 25-28 and 29-35 wherein two different embodiments of valves which reduce likelihood of inadvertent triggering are disclosed.

Embodiment One

Figure 25:
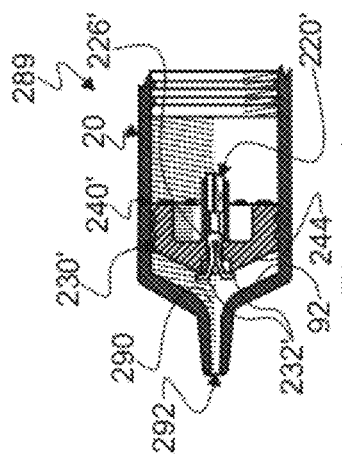
FIG. 25 is a cross section of a latching plunger valve disposed in a syringe.

In a first embodiment (multi-chamber syringe 289), seen in FIG. 25, a stem 220' is provided with a pair of feet (both numbered 232', see also FIG. 28) which are sized and shaped to latch against a distal face 244 of valvular plunger 230', plunger 230' being similar in size and shape to plunger 230, seen in FIG. 12. Referring to FIG. 28, feet 232' are spread apart by molding of associated legs 222". Legs 222" are biased apart from a living hinge 280 to spread feet 232' into a latching state seen in FIG. 25, into contact with a proximally facing, distal face 244 of an associated valvular plunger 230'. Note, in FIG. 25, feet 232 are securely latched against valvular plunger face 244.

Figure 26:
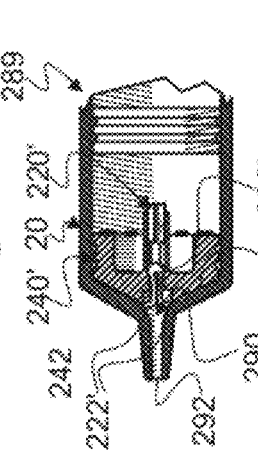
FIG. 26 is a cross section of the plunger valve and syringe seen in FIG. 25 with the plunger valve distally displaced to medially displace latching parts of an associated valve stem.
Figure 27:
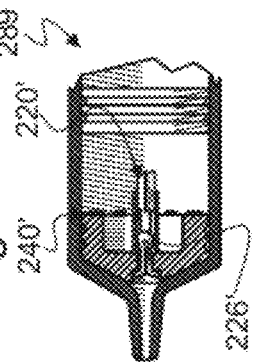
FIG. 27 is a cross section of the plunger valve, similar to the valve seen in FIG. 26, but with the valve stem displaced to open the valve.

As seen in FIG. 26, displacing valve 240' distally into contact with distal face 92 of syringe barrel 20 results in medial displacement of legs 222' due to continuous reduction in size of filleted opening 290 of fluid dispensing orifice 292. It should be noted that using latching of legs 222' requires stem 220' to only be disposed far enough into channel 226 to obstruct fluid passage there through, rather than the necessity for providing total stability for a stem as required by valve 240 (see FIGS. 13-16). Thus, when legs 222' are adequately displaced, stem 220' is expelled from valvular plunger 230' by contraction of plunger material about pathway 242 squeezing and expelling bulbous portion 226' of stem 220'. Stem 220' is further seen in a fully expelled state in FIG. 27 (thus opening valve 240'). Valve stem 220' is seen magnified in FIG. 28. Note living hinge indents 292 which permit facile medial displacement of legs 222" upon contact with a filleted surface (e.g. syringe internal face 92).

Embodiment Two

Reference is now made to FIGS. 29-35 wherein the second embodiment is seen (i.e. valve 240"). The second embodiment may employ a stem 220, as disclosed supra (see FIG. 21), but having a length which conforms to application requirements as disclosed hereafter. As seen in FIG. 29, ring 260' is similar to ring 260 (see FIG. 23) but may have a longer tube 262 to provide full cavity length for cylindrical support, for valvular plunger 230".

Valvular plunger 230", rather than being substantially rigid in construction as in other embodiments disclosed herein, has an arcuate, flexible, concentric thinned section 310 between a cylindrical outer wall 300 and a hollow tubular portion 270' which provides a pathway to a liquid only zone. Portion 310 is thinned sufficiently to be compliant and flexible when acted upon by a differential pressure. As an example, if made from butyl rubber, section 310 may be 0.040 to 0.050 inches thick for a plunger employed in a 30 ml syringe. Valvular plunger 230" is molded as seen in FIG. 29 with portion 310 disposed about hollow tubular portion 270' which provides a channel or pathway 330 from a liquid only zone to a dispensing orifice 252 (see FIG. 30) of an associated multi-chamber syringe 10".

From distal to proximal openings, a liquid pathway 330 is defined by an opening 332 having a diameter sized to permit access to feet 232 (see FIG. 30), and a subsequent channel 334 diametrically sized to tightly bind about a bulbous portion 226' of stem 220 and having a length which securely anchors bulbous portion 226' in place until valvular plunger portion 310 is fully engaged with a syringe barrel internal distal face 92 (as seen in FIG. 33). Proximal to portion 334 liquid pathway 330 is enlarged to permit fluid to be dispensed about stem 220 and thereby from syringe 10" when stem is fully displaced proximally.

As seen in FIG. 30, valvular plunger 230" retains stem 220 in place as valve 240" is displaced without contacting face 92 within syringe barrel 20. When first contact is made between valvular plunger 230" and face 92, as seen in FIG. 31, stem 220 does not yet make contact with face 92.

However, with subsequent distal displacement of plunger 230", feet 232 contact face 92 and distal travel of stem 220 is terminated (see FIG. 32). As valvular plunger 230" is displaced still further distally, portion 310 is forced to conform (nest) with face 92 as seen in FIG. 33. At this point, portion 334 is displaced distally sufficiently far to release bulbous portion 226' and due to elastic memory of portion 334, expel stem 220 proximally, as seen in FIG. 34. Such release exposes duct 224' and opens valve 240". Equalizing distal and proximal pressures about an open valve 240" permits plunger 230" to resume its original shape and displace stem 220 further proximally as seen in FIG. 35.

This embodiment of valve 240" is considered to have an advantage over previously disclosed embodiments by permitting a distal portion of a plunger to make contact with an end of a syringe barrel before contact is made by an associated stem. As seen in FIG. 29A, feet 232 of stem 220 are disposed within a contact zone of a syringe barrel as depicted by dashed lines 300 Such action reduces likelihood of inadvertent triggering of a valve.

Luer Interfacing Valves for Mixing and Sequential Delivery

Three applications for luer interfacing valves are disclosed hereafter, one for a mixing syringe application, one for a sequential delivery syringe application and an application which may be both mixing and sequential delivery providing a saline-dose-saline (SDS) sequential delivery. Attention is drawn to FIGS. 36-56 wherein disclosure of the three applications is provided.

The Mixing Syringe Application

Figure 36:
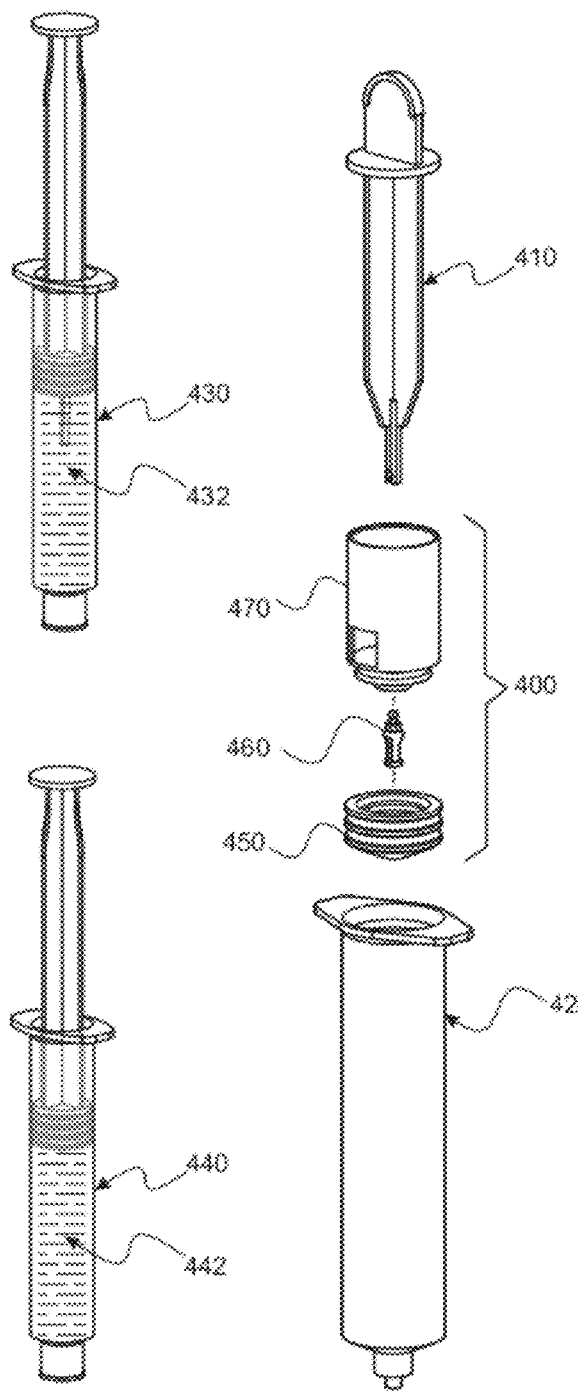
FIG. 36 is a perspective of a group of syringe parts used in an assembly for mixing and flushing.
Figure 37:
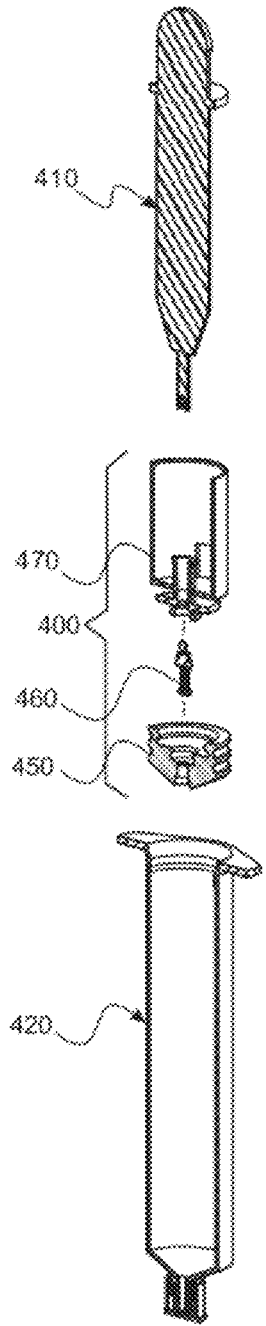
FIG. 37 is a cross section of one set of parts in the group seen in FIG. 36, the group comprising a syringe barrel, a plunger part, a valve stem, a luer fitting adapter and a stem puller.

Components for a mixing syringe application seen in FIG. 36 are a valve assembly 400, seen in exploded view, a valve stem puller 410, an associated syringe barrel 420, a diluent providing syringe 430 and a flush syringe 440. As examples, a diluent syringe 430 may be filled with a desired volume of prescribed diluent 432. Likewise, a flush syringe 440 may be filled with a desired volume of a flush solution 442, such as saline. Generally, a diluent syringe 430 differs from a flush syringe 440 by structure within the diluent syringe for resetting a valve, as disclosed in detail hereafter. For better visualization, valve assembly 400, stem puller 410 and associated barrel 420 are seen in cross section in FIG. 37.

Valve assembly 400 comprises a valvular plunger 450, a valve stem 460 and a luer fitting adapter 470. Valve stem 460 seen in magnified format in FIG. 38 is similar to valve stem 220 (see FIG. 21), but changed at the proximal end to provide for an interface with stem puller 410. As seen in FIG. 38, stem 460 comprises a bulbous portion 226', legs 222', and feet 232 which combine to form a duct 224' all similar in form and function to the same parts of stem 220. However, on a proximal end 472, stem 460 comprises a connecting (latching) interface 474 by which stem 460 is releasably affixed to stem puller 410, a magnified portion of which is seen in FIG. 39. As best seen in FIG. 39A, when stem puller 410 is oriented in a first angular orientation with stem 460, edges 476 of interface 474 latch upon complimentary edges 478 of stem puller 410 to securely affix stem 460 to puller 410. Mode for release of the connecting interface is disclosed in detail hereafter.

Reference is now made to FIGS. 41-43 wherein an exemplary series of steps for assembly of valve 400 and attachment to stem puller 410 is seen. Note that luer fitting adapter 470 has a medially disposed female luer fitting 480. Luer fitting 480 has an outlet orifice 482 at a distally disposed base 484. The form of orifice 482 is better seen in FIG. 40. In this case, orifice 482 is octagonal in shape. While it is not necessary for the shape to be octagonal, it is important that the shape deter rotation of a rod 486 associated with that portion 488 of puller 410 which interfaces with stem 460. Thus, when stem 460 is securely affixed within valvular plunger 450 to close valve 400 and stem puller 410 is disposed within orifice 482 and affixed to stem 460 as seen in 39A, puller 410 cannot be rotated relative to stem 460 to free the connecting interface with stem 460.

Thus, to assemble stem puller 410 to stem 460, rod 486 is inserted through orifice 482 in luer fitting 480 and affixed to stem 460 as seen in FIG. 42. Note that luer fitting adapter 470 has a mounting ring 490 disposed for being securely affixed to valvular plunger 450. Valvular plunger 450 has a through hole 492 having the same valve closure constriction as valvular plunger 300 (see decreased diameter channel 242 in FIG. 13). Thus when bulbous portion 226' (see FIG. 38) is disposed within channel 492, valve 400 is closed or reset. Valvular plunger 450 has an annular groove 494 disposed to securely and tightly engage ring 490 of luer adapter 470. Therefore, the final assembly step for valve 400 is displacing valvular plunger 450 about stem 460 and engaging groove 494 about ring 490. (See FIG. 43.) Further, it should be noted that valvular plunger 450 does not have a tube medially affixed for access to a liquid only zone. Having a luer fitting which provides access to a syringe (which is air purgeable) eliminates the need for such a tube.

An assembled valve 400 and affixed stem puller 410 disposed within a conventional syringe barrel 500 is seen in FIG. 44. Note that the valve 400 is closed and, with a cap 510 affixed to the barrel 600, a closed distal chamber 520 is provided thereby. Matter 530 provided for mixing (or dilution) is generally disposed within this closed chamber 520 providing a package 540 in which matter 530 can be stored and transported prior to mixing or dilution to be made ready for dispensing.

As seen in FIG. 45, preparatory for mixing (diluting), the stem puller 410 is first pulled in direction of arrow 542; then, when portion 488 of rod 486 clears orifice 482, stem puller 410 is rotated about 90° in either direction to unlatch puller 410 from stem 460. (Note, at this point, stem 460 is displaced in direction of arrow 546, as seen in FIG. 46, to open valve 400.) Puller 410 is then removed from barrel 500.

With puller 410 removed, as seen in FIG. 47, a syringe 430 containing a diluent 432 is inserted into barrel 500 and affixed to luer fitting 480 (see FIG. 48). Note, plunger 570 of plunger assembly 572 of syringe 430 has an elongated medially disposed protuberance 574. Plunger 570 is better seen in FIG. 49. Along the length of protuberance 574 is a linear slot 576 which provides a pathway for liquid as protuberance 574 is displaced through orifice 482 (see FIG. 40) and luer fitting 480. For, as syringe 430 is emptied permitting fluid 432, initially resident in syringe 430 to be delivered into distal chamber 520 (see FIG. 50), plunger 570 is displaced to deliver protuberance 574 into contact with stem 460. Stem 460 is resultingly displaced until duct 224' (see FIG. 38) is occluded. Once duct 224' is occluded, further displacement of plunger 570 resets valve 400. Of particular note, protuberance 574 should be sufficiently rigid to displace stem 460 to close valve 400. Note also that protuberance 574 may be replaced by a rod (not shown) disposed within the exit orifice 578 (see FIG. 48) of diluent syringe 430.

Dispensing fluid from syringe 430 causes proximal displacement of valve 400 across a section of the inner wall 581 of barrel 500 which, unless protected, would be subject to contamination from the exterior of a syringe inserted to connect to luer fitting 480. To protect against such contamination, a hollow cylindrical sleeve 580 is affixed to luer fitting adapter 470 to act as a shield for the inner wall of syringe 500. Note portals 582 (see FIGS. 48 and 50) used for molding access to female luer fitting 480. Luer fitting adapter 470 may be injection molded of materials, such as polypropylene or other products which are injection moldable and used for making luer fittings.

With diluent 432 fully dispensed from syringe 430, as seen in FIG. 50, valve 400 is closed and a mixing procedure may be consummated. Syringe 430 is then displaced from barrel 500 as seen in FIG. 51. For flushing, a second syringe 440 may be inserted into barrel 500 and affixed to valve 400 to provide an assembly 600 as seen in FIG. 52. Per standard procedure, assembly 600 may be inverted, as seen in FIG. 53 and gas purged from distal chamber 520. Per facility protocol, contents of chamber 520 are dispensed, as seen in FIG. 54. Then, valve 400 is opened and contents 442 of syringe 440 are dispensed as desired. An empty syringe 440 and chamber 520 following sequential delivery is seen in FIG. 55.

Sequential Delivery

Within the scope of the instant invention, a sequential delivery syringe is a simple subset of the mixing syringe disclosed supra. Reference is made to FIGS. 52-55 once more. As seen in FIG. 52, distal chamber 520 may be filled using conventional syringe filling techniques. Either a pre-purged, filled syringe 440 or a prime-free syringe, used as a flush or second delivered solution source, is affixed to valve 400. Distal chamber 520 may be purged (see FIG. 53). Then, contents of assembly 600 are dispensed first, by emptying distal chamber 520 (see FIG. 54), and by subsequently dispensing fluid 442 from syringe 440 after valve 400 is opened (see FIG. 55). Note, for this mode of dispensing, only one plunger (associated with a valve or a plunger assembly of a smaller syringe) is displaced at any one time.

It is critical to note that a sequential delivery syringe may be effectively used for dispensing antineoplastic or other hazardous drugs with the proximal chamber providing for a drug clearing flush at the end of a drug delivery procedure. However, it should also be noted that careful consideration should be paid when displacing such drugs into the proximal chamber. For this purpose it is recommended that a dripless connector (not shown) be affixed to the male luer-lock entry orifice of the syringe to avert undesired and potentially hazardous emissions and spills. Such a dripless connector should be securely affixed so that an inadvertent disconnection does not produce a dangerous discharge.

SDS Sequential Delivery

Reference is now made to FIG. 56 in which a SDS sequential delivery system 700 is seen. As seen in FIG. 56, system 700 comprises a syringe barrel 710 (which is similar to barrel 500) in which a first valve 720 is seen distally disposed relative to a second valve 730. Each valve 720 and 730 has a stem 740 and 740', respectively, which is similar to stem 220 (see FIG. 21), but without more proximal parts 220 and 230. Even so, each stem 740 and 740' is enclosed within a channel 750 and 750' of valvular plungers 760 and 760' of valves 720 and 730, respectively, and open and close each associated valve in the same manner as stem 220 is displaced to an open state. Valvular plunger 760 comprises a proximal surface 770 which is convex and which is sized and shaped to nest with a corresponding concave surface 770' of valvular plunger 760'. Further, valvular plunger 760 comprises a portion 772 of surface 770 which is sufficiently rigid to provide for activating stem 740 of valvular plunger 760' upon collision therewith.

Each valvular plunger 760 and 760', so disposed provides a most distal chamber 774 and a more proximal chamber 776 within barrel 710. A through hole 778 provides a pathway for fluid to be dispensed from chamber 776 when valve 720 is open. A cap 780 provides a removable distal closure for barrel 710.

Valvular plunger 760' comprises an interface for a luer fitting adapter 470 (see FIG. 41). Thus, a dilution syringe 430 or a flush syringe 440 can be affixed to provide an additional chamber for assembly 700. Uses of syringes 430 and 440 are disclosed in detail supra for mixing and sequential delivery.

In FIG. 56, a flush syringe 440 is seen filled with flush solution 442 and assembly 700 is fully prepared for SDS dispensing to a patient. If assembly 700 would have been earlier prepared by mixing a solution in chamber 776, valve 730 would have been opened (for example by a stem puller 410 (see FIG. 45) and a diluent dispensed into chamber 776 from a diluent syringe 430 (see FIG. 48). Following diluent dispensing, valve 730 is closed via a protuberance, which acts as protuberance 574 (see FIG. 48). Syringe 430 is then replaced by syringe 440 as seen in FIG. 56 for sequential liquid dispensing.

For four of the different valves and related multi-chamber embodiments are disclosed herein, the following table is provided as an aid for helping to discern features of one valve compared to the others.

TABLE

Valve features comparison

| Element | Valve 240 | Valve 240' | Valve 240" | Valve 400 |
|---|---|---|---|---|
| Plunger | Rigid construction designed to nest with syringe face | Rigid construction designed to nest with syringe face | Pliant distal face molded to provide plunger impact before stem impact with syringe face and to be deformed to nest with syringe face | Rigid construction designed to nest with syringe face |
| Stem | Rigid, feet, rear plunger interface, duct opening disposed to permit valve closure before stem contact with syringe | Flexible legs affixed to feet, rear plunger interface, duct opening disposed to permit valve closure before stem contact with syringe | Rigid, feet, rear plunger interface, duct opening disposed to permit valve closure before stem contact with syringe | Rigid, feet, rear plunger interface, duct opening disposed to permit valve closure before stem contact with syringe |
| Ring/Support Interface | Yes, with plunger tube support | Yes, with plunger tube support | Yes, with a longer plunger tube support than for valves 240 and 240' | Yes, a luer fitting whereby a barrel of a smaller syringe is inserted into a barrel of a larger syringe to communicate through the valve toward a distal chamber housed within the larger syringe barrel |
| Resettable (?) | Yes | Yes | Yes | Yes |
| Rear Chamber fillable (?) | Yes | Yes | Yes | Yes, via replaceable syringes |
| Plunger tube Access to Liquid Only Zone | Yes | Yes | Yes | No, unnecessary because gas can be purged from proximal chamber 776 |

All of valves (240, 240', 240" and 400) included in the table above differ from the valve disclosed in Thorne 862 as follows:
1. Valve 240" has a deformable medial section; the valve of Thorne 862 is of rigid construction.
2. The stem of each valve 240, 240' and 240" is shortened and has a duct opening distally displaced from a plane through the widest diameter of the bulbous part (not so, for the valve of Thorne 862). Such is necessary for resetting a valve from an open to a closed state as a stem which collides with the associated face of a syringe would not permit duct closure. Also, stem of valves 240, 240' and 240" have a series of proximally disposed wings for internal support of a plunger tube to a liquid only zone.
3. The ring of each valve 240, 240' and 240" comprises an inner ring which provides support for the plunger tube compared with the valve of Thorne 862 for which no such ring is taught, but which is necessary for valve resetting.
4. The ring attachment of valve assembly 400 comprises a luer fitting whereby the rear chamber is provided by a second syringe having a barrel which is insertable into the barrel of a larger syringe in which the distal chamber is disposed.
5. Apparatus and methods disclosed herein provide for facilely filling or replacing a rear chamber. No such apparatus or method is taught in Thorne 862.

Inventions disclosed herein may be embodied in other specific forms without departing from the spirit or essential characteristics thereof. The present embodiments are therefore to be considered in all respects as illustrative and not restrictive, the scope of this invention being indicated by the appended claims rather than by the foregoing description, and all changes which come within the meaning and range of equivalency of the claims are therefore intended to be embraced therein.

What is claimed and desired to be secured by Letters Patent is:

1. A method for filling a proximally disposed chamber of an assembled medical syringe comprising structure which defeats efficacious filling of that chamber through the distal orifice of the syringe, said method comprising the steps of:
    (a) providing a medical syringe comprising:
        (i) a conventional syringe barrel having a substantially constant diameter inner wall about a medial axis and closed at one end except for an orifice through which fluid is communicated to and from the barrel, said barrel being open at the other end for introduction of a plunger of a plunger assembly used to displace fluid disposed within the barrel, introduction of the plunger closing the barrel to form the proximally disposed chamber;
        (ii) the plunger assembly comprising the plunger having a cylindrically shaped exterior sidewall sized and shaped for wiping fluid from the inner wall as it is displaced there along and a medially disposed through hole;

(iii) said plunger assembly further comprising a plunger shaft comprising a plunger interface on a distal end by which the plunger is securely affixed to said shaft and a medially disposed through hole oriented parallel to the medial axis of the syringe and in line with said plunger hole and a close-able fitting on the proximal end for connecting a fluid source to the communicating pathway;

(iv) providing a cap which provides closure for the fitting;

(v) providing a valve disposed between the plunger of the plunger rod assembly and the closed one end to provide a proximal chamber and a distal chamber of a dual chamber syringe;

(vi) providing a linearly displaceable and thereby resettable stem within a valvular plunger as part of the valve, the stem being disposed in a first state to close the valve and displaced to a second state to open the valve, thereby permitting fluid to be dispensed from the proximal chamber;

(b) assembling the syringe by:

(i) inserting the plunger of said plunger rod assembly into the barrel to provide the accessible proximal chamber of the syringe;

(ii) assuring the cap is displaced from said interface;

(iii) connecting a fluid source to said interface;

(iv) dispensing a predetermined volume of liquid into the proximal chamber; and (v) closing the pathway with the cap; and (c) after filling both proximal and distal chambers performing the following steps:

(i) sequentially dispensing liquid from both chambers while retaining gas resident in the proximal chamber;

(ii) simultaneously applying a position retaining force to the plunger of the plunger rod assembly which is communicated to the stem of the valvular stopper to first provide forced closure of the valve and then applying a concurrent pressure from a pressurized source through the orifice thereby displacing the stem from the second state to the first state, thereby closing the valve.

2. A method according to claim 1 wherein the dispensing step comprises displacing the valve as liquid is dispensed into the proximal chamber.

3. A method according to claim 1 wherein said dispensing step comprises drawing excess gas from said proximal chamber.

* * * * *